(12) United States Patent
Zemlok et al.

(10) Patent No.: US 11,510,747 B2
(45) Date of Patent: Nov. 29, 2022

(54) ROBOTIC SURGICAL SYSTEMS AND DRAPES FOR COVERING COMPONENTS OF ROBOTIC SURGICAL SYSTEMS

(71) Applicant: Covidien LP, Mansfield, MA (US)

(72) Inventors: Michael Zemlok, Prospect, CT (US); Chi Min Seow, New Haven, CT (US); Mark MacLeod, Southbury, CT (US); Jaimeen Kapadia, Cambridge, MA (US); Richard Lech, Hamden, CT (US)

(73) Assignee: Covidien LP, Mansfield, MA (US)

( * ) Notice: Subject to any disclaimer, the term of this patent is extended or adjusted under 35 U.S.C. 154(b) by 371 days.

(21) Appl. No.: 16/616,217

(22) PCT Filed: May 7, 2018

(86) PCT No.: PCT/US2018/031301
§ 371 (c)(1),
(2) Date: Nov. 22, 2019

(87) PCT Pub. No.: WO2018/217430
PCT Pub. Date: Nov. 29, 2018

(65) Prior Publication Data
US 2020/0093556 A1    Mar. 26, 2020

Related U.S. Application Data

(60) Provisional application No. 62/510,883, filed on May 25, 2017.

(51) Int. Cl.
*A61B 46/10* (2016.01)
*A61B 34/35* (2016.01)
*A61B 50/13* (2016.01)

(52) U.S. Cl.
CPC .............. *A61B 46/10* (2016.02); *A61B 34/35* (2016.02); *A61B 50/13* (2016.02)

(58) Field of Classification Search
CPC .................................................. B25J 19/0054
See application file for complete search history.

(56) References Cited

U.S. PATENT DOCUMENTS

3,528,720 A   9/1970   Treace
3,540,441 A   11/1970  Collins
(Continued)

FOREIGN PATENT DOCUMENTS

JP   H03205049   9/1991
JP   H04092656   3/1992
(Continued)

OTHER PUBLICATIONS

Vertut, Jean and Philippe Coiffet, Teleoperation and Robotics: Evolution and Development, English translation Prentice-Hall, Inc., Inglewood Cliffs, NJ, USA, 1986 (Abstract Only).
(Continued)

*Primary Examiner* — Scott Luan

(57) ABSTRACT

A drape for covering a robotic surgical system includes a first end portion, a second end portion, and an intermediate portion extending between the first and second end portion. The first end portion defines a cavity therein and has an outer surface and an inner surface and defines an inlet through the outer and inner surfaces. The cavity is dimensioned for receipt of an instrument drive unit and is in fluid communication with the inlet. The second end portion has an outer surface and an inner surface and defines an outlet through the outer and inner surfaces. The second end portion defines a cavity therein that is in fluid communication with the outlet. The intermediate portion defines an elongated conduit therethrough dimensioned for receipt of a surgical robotic arm.

18 Claims, 22 Drawing Sheets

(56) References Cited

U.S. PATENT DOCUMENTS

| | | |
|---|---|---|
| 3,707,964 A | 1/1973 | Patience et al. |
| 3,747,655 A | 7/1973 | Hadtke |
| 3,777,749 A | 12/1973 | Collins |
| 3,952,738 A | 4/1976 | Krzewinski |
| 3,955,569 A | 5/1976 | Krzewinski et al. |
| 4,457,026 A | 7/1984 | Morris |
| 4,919,112 A | 4/1990 | Siegmund |
| 5,515,868 A | 5/1996 | Mills |
| 5,522,403 A | 6/1996 | Bark et al. |
| 5,740,699 A | 4/1998 | Ballantyne et al. |
| 5,860,420 A | 1/1999 | Wiedner et al. |
| 5,957,831 A | 9/1999 | Adair |
| 6,105,578 A | 8/2000 | Sommers et al. |
| 6,116,741 A | 9/2000 | Paschal |
| 6,123,080 A | 9/2000 | Mohan et al. |
| 6,132,368 A | 10/2000 | Cooper |
| 6,206,903 B1 | 3/2001 | Ramans |
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,346,072 B1 | 2/2002 | Cooper |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll et al. |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,923,186 B2 | 8/2005 | Gavette et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,025,064 B2 | 4/2006 | Wang et al. |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco et al. |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 7,992,560 B2 | 8/2011 | Burton et al. |
| 8,002,767 B2 | 8/2011 | Sanchez et al. |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |

(56) References Cited

U.S. PATENT DOCUMENTS

| | | |
|---|---|---|
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,813,755 B2 | 8/2014 | Hoffmann |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart et al. |
| 8,989,903 B2 | 3/2015 | Weir et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,019,345 B2 | 4/2015 | O |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,629,680 B2 | 4/2017 | Winer |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |

(56) References Cited

U.S. PATENT DOCUMENTS

| | | |
|---|---|---|
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 2003/0106493 A1 | 6/2003 | Christian et al. |
| 2005/0161176 A1 | 7/2005 | Brenner et al. |
| 2006/0161138 A1 | 7/2006 | Orban, III |
| 2006/0199999 A1 | 9/2006 | Ikeda et al. |
| 2008/0065105 A1 | 3/2008 | Larkin et al. |
| 2011/0041995 A1 | 2/2011 | Adams |
| 2011/0259347 A1 | 10/2011 | Zurn |
| 2015/0047647 A1 | 2/2015 | Winer |
| 2015/0202009 A1 | 7/2015 | Nussbaumer et al. |
| 2016/0038013 A1* | 2/2016 | Czupalla .............. A61B 1/04 600/123 |
| 2017/0360516 A1* | 12/2017 | Hares .................. A61B 34/30 |

FOREIGN PATENT DOCUMENTS

| | | |
|---|---|---|
| JP | 2009509653 A | 3/2009 |
| WO | 8501496 A1 | 4/1985 |
| WO | 9832391 A1 | 7/1998 |
| WO | 2015080148 A1 | 6/2015 |
| WO | 2016079532 A1 | 5/2016 |
| WO | 2016146993 A1 | 9/2016 |
| WO | 2016196165 A1 | 12/2016 |
| WO | 2017015207 A1 | 1/2017 |

OTHER PUBLICATIONS

European Search Report dated Jan. 21, 2021, issued in corresponding EP Appln. No. 18806411, 7 pages.
Japanese Office Action dated Dec. 15, 2021, issued in corresponding JP Appln. No. 2019562607, 8 pages.
Chinese Office Action dated May 31, 2022, issued in corresponding CN Appln. No. 201880029804, 11 pages.

* cited by examiner

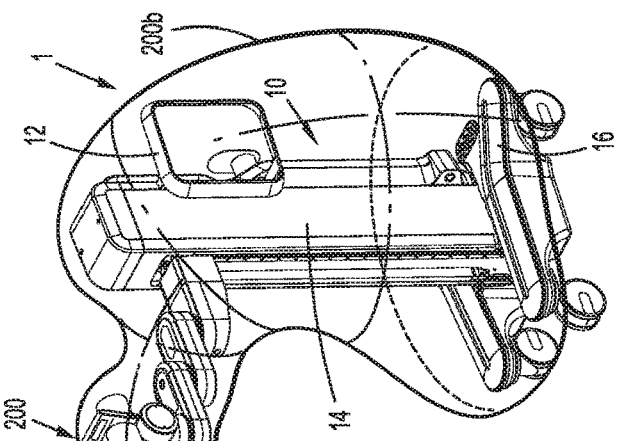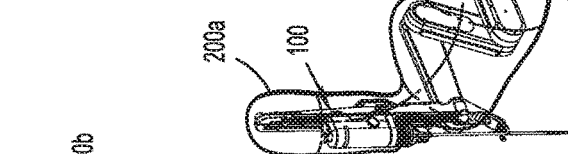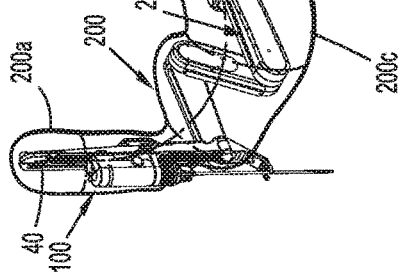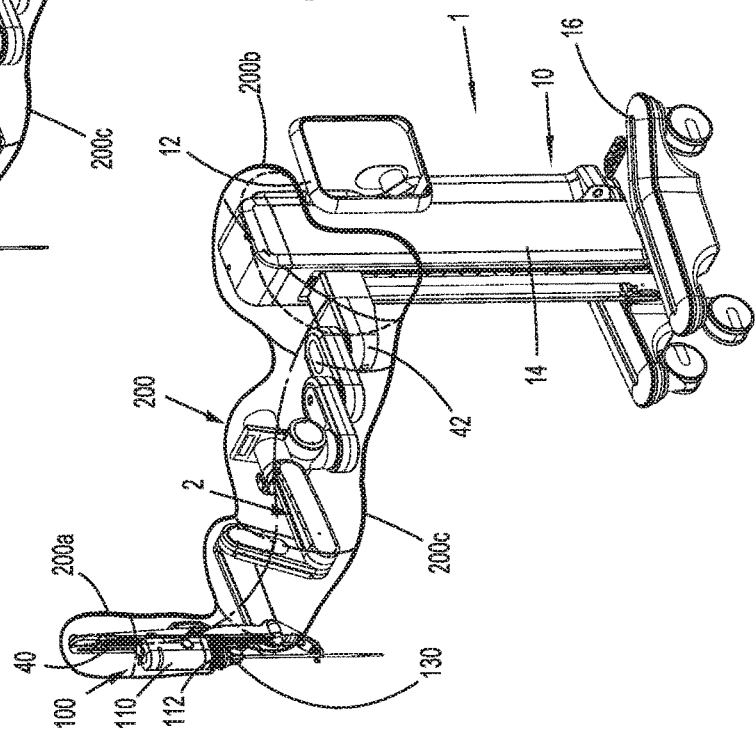
FIG. 4A
FIG. 4B
FIG. 4C

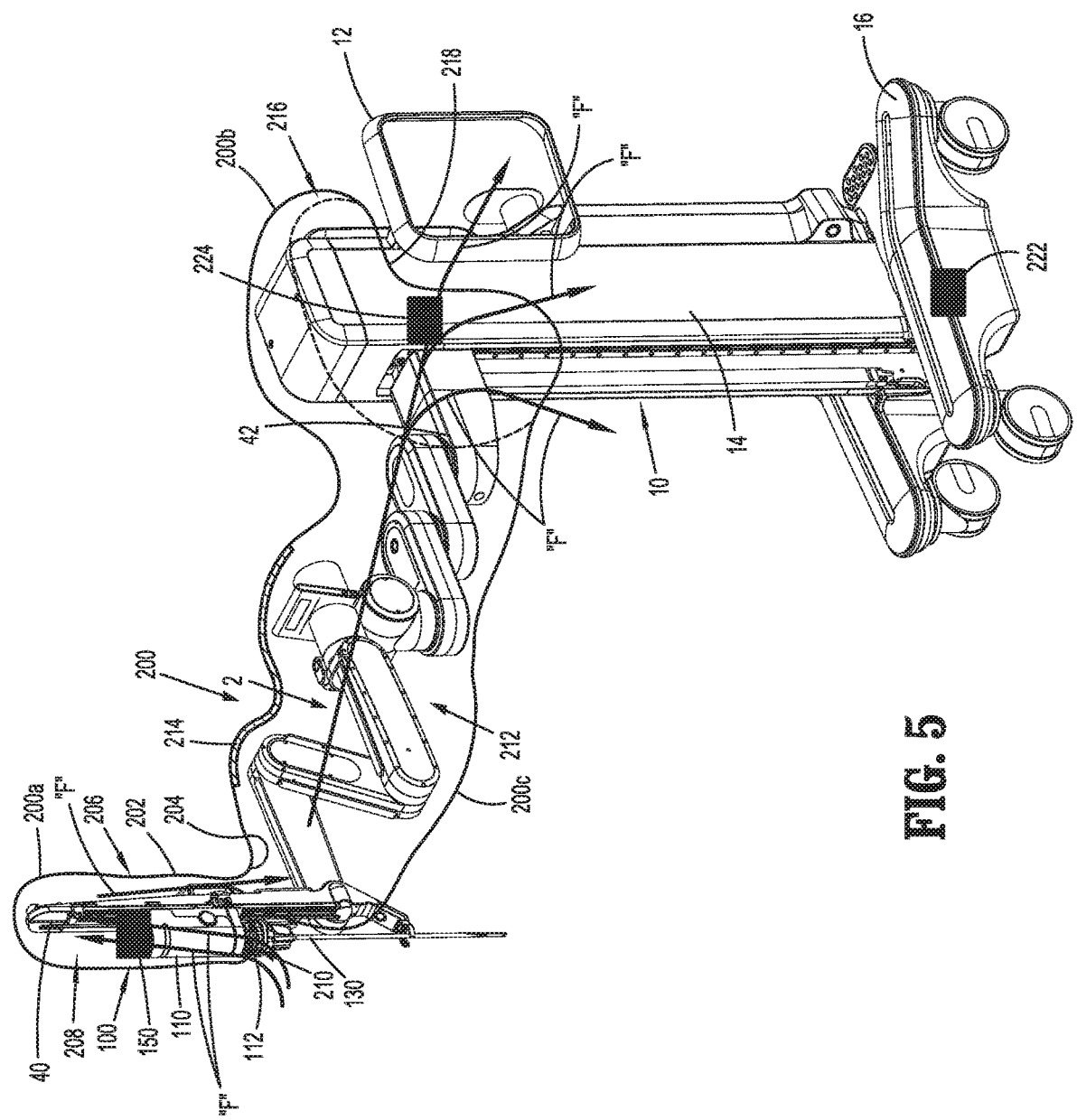

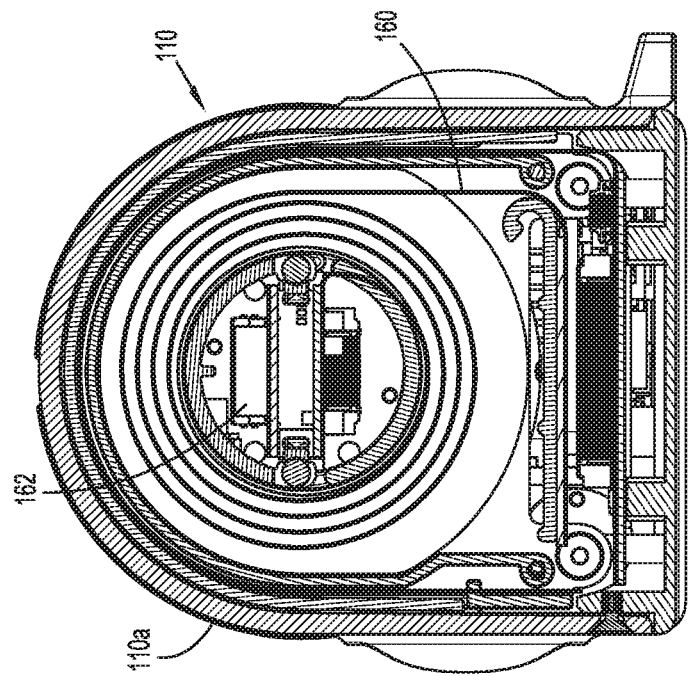
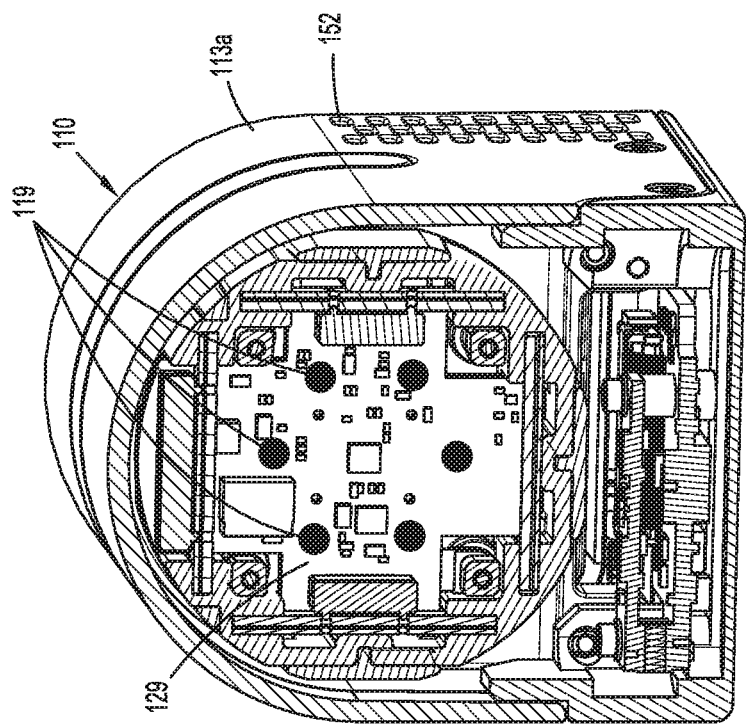
FIG. 15D
FIG. 15C

ROBOTIC SURGICAL SYSTEMS AND DRAPES FOR COVERING COMPONENTS OF ROBOTIC SURGICAL SYSTEMS

BACKGROUND

Robotic surgical systems have been used in minimally invasive medical procedures. Some robotic surgical systems include a console supporting a surgical robotic arm and a surgical instrument, having at least one end effector (e.g., forceps or a grasping tool), mounted to the robotic arm. The robotic arm provides mechanical power to the surgical instrument for its operation and movement.

Manually-operated surgical instruments often included a handle assembly for actuating the functions of the surgical instrument. However, when using a robotic surgical system, no handle assembly is typically present to actuate the functions of the end effector. Accordingly, to use each unique surgical instrument with a robotic surgical system, an instrument drive unit is used to interface with the selected surgical instrument to drive operations of the surgical instrument.

The operation of an instrument drive unit, robotic arm, robotic cart, and/or other components of the robotic surgical system generates heat. An excess of heat may damage or impair the functioning of various components of the instrument drive unit or other components of the robotic surgical system. Accordingly, it would be beneficial to provide a means for cooling the components of the surgical system while also maintaining the sterility of the surgical system.

SUMMARY

In accordance with an aspect of the present disclosure, a drape for covering and facilitating cooling of a robotic surgical system is provided. The drape includes a first end portion, a second end portion, and an intermediate portion extending between the first and second end portions. The first end portion has an outer surface and an inner surface and defines an inlet through the outer and inner surfaces. The first end portion also defines a cavity therein. The cavity is dimensioned for receipt of an instrument drive unit and is in fluid communication with the inlet. The second end portion has an outer surface and an inner surface and defines an outlet through the outer and inner surfaces. The second end portion further defines a cavity therein that is in fluid communication with the outlet. The intermediate portion defines an elongated conduit therethrough dimensioned for receipt of a surgical robotic arm.

In some embodiments, the inlet may be annular and dimensioned to surround a sterile interface module.

It is contemplated that the first end portion may include a patch that covers the inlet and is configured to permit ingress of air through the inlet. The patch may be fabricated from a liquid resistant, air-permeable material.

It is envisioned that the first end portion of the drape may include a first flap and a second flap each extending from the outer surface of the first end portion. The first flap may overlap with the inlet to define a first portion of a fluid pathway. The second flap may overlap with the first flap to define a second portion of the fluid pathway. The first and second portions of the fluid pathway may be parallel with one another and in fluid communication with one another. The first end portion may also include a first rib and a second rib. The first rib may be disposed in and extend parallel with the first portion of the fluid pathway to maintain a spacing between the first flap and the outer surface. The second rib may be disposed in and extend parallel with the second portion of the fluid pathway to maintain a spacing between the first and second flaps.

In some embodiments, the first end portion may include a liquid resistant, air-permeable material attached to the outer surface of the first end portion. The liquid resistant, air-permeable material may cover the inlet.

It is contemplated that the second end portion may define a vent through the outer and inner surfaces of the second portion.

In another aspect of the present disclosure, a robotic surgical system is provided and includes a surgical robotic arm, a surgical assembly coupled to a first end portion of the surgical robotic arm, and a drape for covering the surgical robotic arm and the surgical assembly. The drape includes a first end portion, a second end portion, and an intermediate portion extending between the first and second end portions. The first end portion has an outer surface and an inner surface and defines an inlet through the outer and inner surfaces. The first end portion further defines a cavity therein. The cavity is dimensioned for receipt of the surgical assembly and is in fluid communication with the inlet. The second end portion has an outer surface and an inner surface and defines an outlet through the outer and inner surfaces. The second end portion further defines a cavity therein that is in fluid communication with the outlet. The intermediate portion defines an elongated conduit therethrough dimensioned for receipt of the surgical robotic arm.

In some embodiments, the surgical assembly may include a fan configured to draw air from a sterile field of a surgery, through the inlet of the drape, into the surgical assembly, out of the drape through the outlet thereof, and away from the sterile field of the surgery. The robotic surgical system may further include a controller in communication with the fan. The controller may be configured to adjust a speed of the fan based on an orientation of the robotic arm. The speed of the fan may be adjusted using measurements taken by strain gauges coupled at joints of the surgical robotic arm. The controller may also be configured to adjust a speed of the fan based on thermal sensors, current sensors, and/or tachometers and/or encoders within the fan.

It is contemplated that the robotic surgical system may further include a vent attached to the drape. The controller may be further configured to move the vent between open and closed configurations based on a temperature within the drape and/or a speed of a fan.

It is envisioned that the surgical assembly may include an instrument drive unit having a first end portion and a second end portion. A fan may be attached to the first end portion. The surgical assembly may include a sterile interface module coupled to the second end portion of the instrument drive unit. The sterile interface module may be configured to be surrounded by the inlet of the drape to permit air to pass into the cavity of the first end portion of the drape via the sterile interface module. The instrument drive unit may have a plurality of fluid channels extending from the first end portion of the instrument drive unit to the second end portion of the instrument drive unit. The fluid channels may take a tortuous pathway through the instrument drive unit such that ingress of liquids is prevented and ingress of air is allowed. In some embodiments, the robotic surgical system may further include a robotic cart having a first end portion and a second end portion. The cavity of the second end portion of the drape may be dimensioned to receive at least one of the first or second end portions of the robotic cart. The robotic cart may have a fan that directs air flow in a direction from the first end portion of the drape toward the second end portion of the drape through the conduit of the drape.

It is contemplated that the drape may include an elongated conductive rib extending along an inner surface of the intermediate portion of the drape.

It is envisioned that the inlet of the drape may be annular and dimensioned to surround a distal end portion of an instrument drive unit of the surgical assembly.

In some embodiments, the first end portion of the drape may include a patch covering the inlet and configured to permit ingress of air through the inlet. The patch may be fabricated from a liquid resistant, air-permeable material.

It is contemplated that the first end portion of the drape may include a first flap and a second flap each extending from the outer surface of the first end portion. The first flap may overlap with the inlet to define a first portion of a fluid pathway. The second flap may overlap with the first flap to define a second portion of the fluid pathway. The first and second portions of the fluid pathway may be parallel with one another and in fluid communication with one another. The first end portion may also include a first rib and a second rib. The first rib may be disposed in and extend parallel with the first portion of the fluid pathway to maintain a spacing between the first flap and the outer surface. The second rib may be disposed in and extend parallel with the second portion of the fluid pathway to maintain a spacing between the first and second flaps.

In some embodiments, the first end portion of the drape may include a liquid resistant, air-permeable material attached to the outer surface of the first end portion. The liquid resistant, air-permeable material may cover the inlet.

It is contemplated that the drape may further include a tubular member extending along the intermediate portion thereof. The tubular member may include a proximal opening disposed within the first end portion of the drape and a distal opening disposed adjacent the second end portion of the drape such that air travels into the tubular member from the first end portion of the drape via the proximal opening and exits the tubular member via the distal opening.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about plus or minus 10 degrees from true parallel and true perpendicular.

BRIEF DESCRIPTION OF THE DRAWINGS

Embodiments of the present disclosure are described herein with reference to the accompanying drawings, wherein:

FIGS. 4A-4C are perspective views of a drape covering the robotic surgical assembly, the robotic arm, and different portions of the robotic arm cart;

FIG. 5 is a perspective view of the robotic surgical assembly, the robotic arm, and the robotic arm cart shown in FIG. 2 each covered by the drape;

FIG. 15C is a cross-sectional view, taken along line 15C-15C of FIG. 13, illustrating air channels defined through yet another portion of the instrument drive unit;

FIG. 15D is a cross-sectional view, taken along line 15D-15D of FIG. 13, illustrating a flex spool assembly of the instrument drive unit;

DETAILED DESCRIPTION

Figure 1:
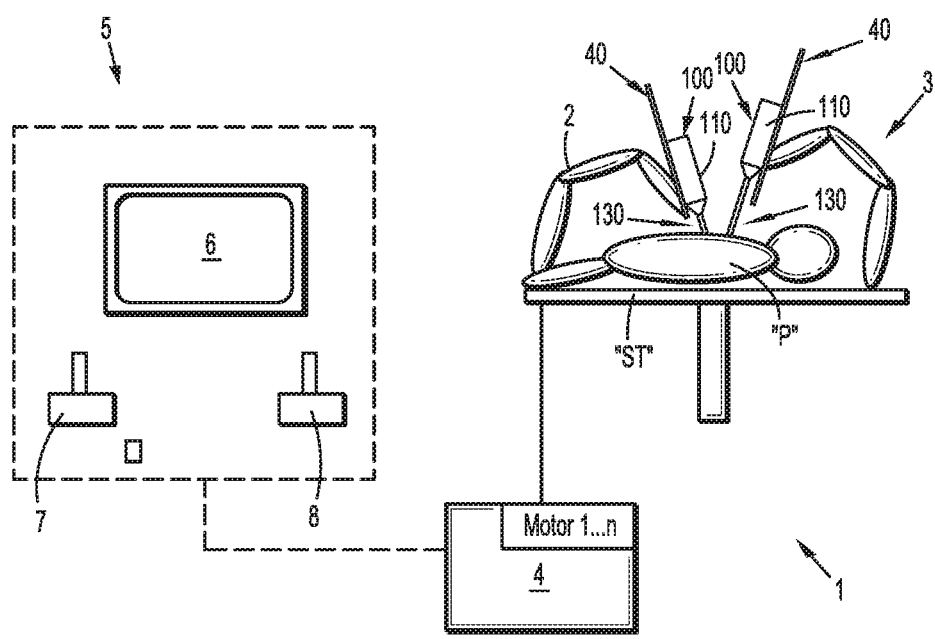
FIG. 1 is a schematic illustration of a robotic surgical system including a robotic surgical assembly in accordance with the present disclosure.

Embodiments of the presently disclosed robotic surgical system including a robotic arm cart, a surgical robotic arm, a surgical assembly (including an instrument drive unit ("IDU") and a surgical instrument), and a drape for covering some or all of the aforementioned components, are described in detail with reference to the drawings, in which like reference numerals designate identical or corresponding elements in each of the several views. As used herein the term "distal" refers to that portion of the robotic arm cart, surgical robotic arm, surgical assembly, or drape, that is closer to the patient, while the term "proximal" refers to that portion of the robotic arm cart, surgical robotic arm, surgical assembly, or drape, that is farther from the patient.

As will be described in detail below, provided is a drape for covering and facilitating cooling various components of a robotic surgical system. The drape maintains sterility of the surgical assembly disposed therein and cools the components thereof by facilitating the transfer of air through the drape and away from the surgical assembly. Further, the surgical assembly includes a fan or fans, heat sinks, and a labyrinth of channels defined through the components of the surgical assembly to facilitate cooling thereof.

Figure 2:
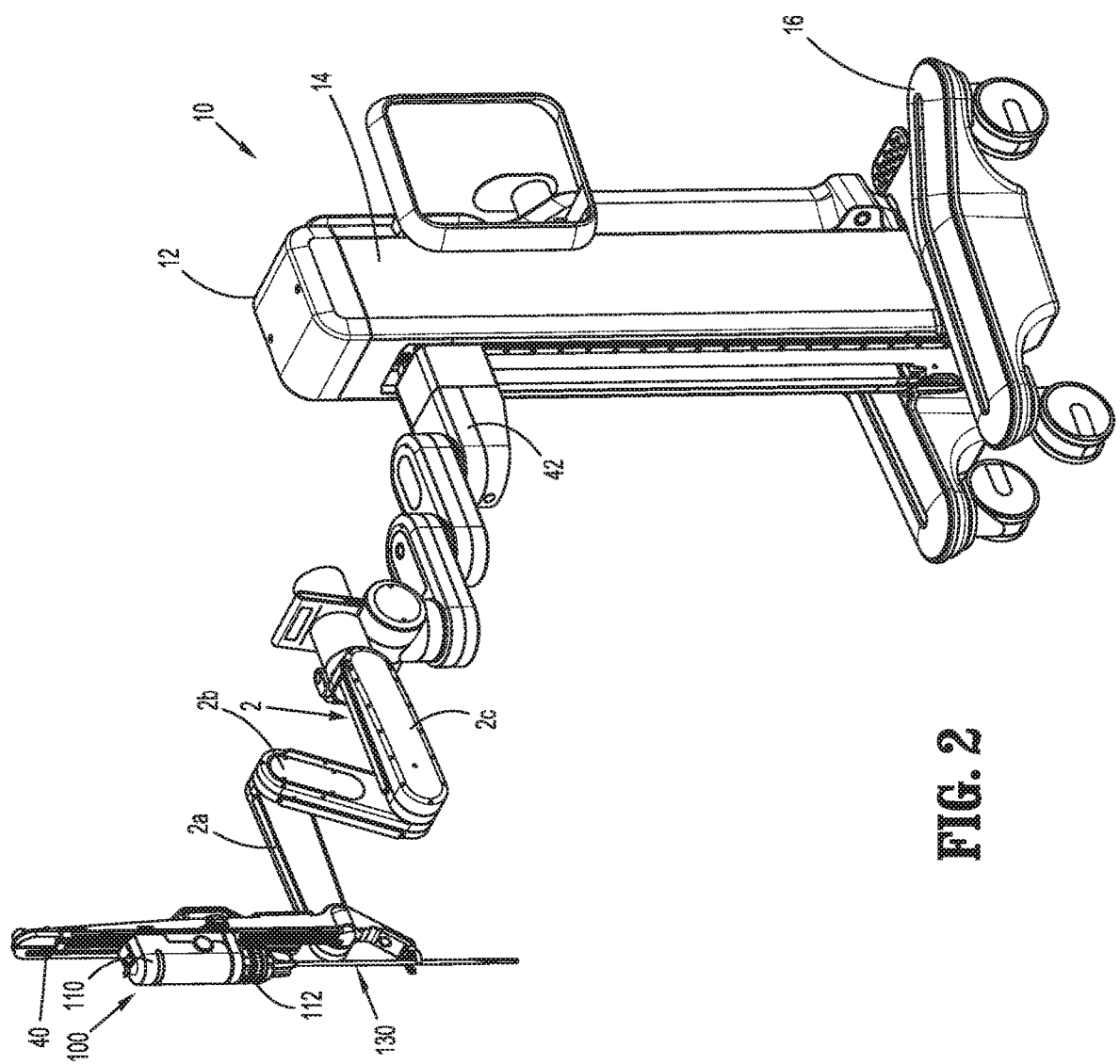
FIG. 2 is a perspective view of the robotic surgical assembly of FIG. 1 attached to a robotic arm, which is attached to a robotic arm cart.
Figure 3:
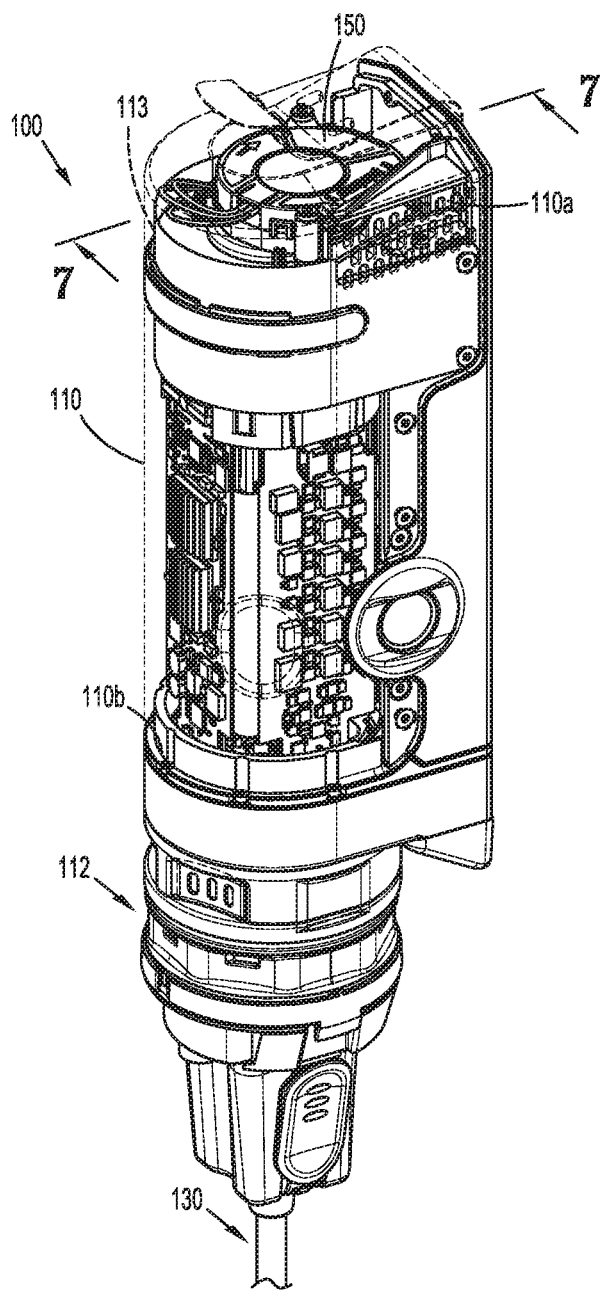
FIG. 3 is a perspective view of the robotic surgical assembly of FIG. 2.

Referring initially to FIGS. 1-3, a surgical system, such as, for example, a robotic surgical system 1, generally includes a robotic arm or robotic arms 2, 3 coupled to a robotic cart 10, a surgical assembly 100 coupled to the surgical robotic arm 2, and a drape 200 (FIGS. 4A-4C) for covering the robotic arm 2 and the surgical assembly 100. In some embodiments, the drape 200 may be dimensioned to also cover the robotic arm cart 10. The surgical assembly 100 includes an instrument drive unit (hereinafter "IDU") 110 coupled to a slide rail 40 of surgical robotic arms 2, 3, and an electromechanical surgical instrument 130 operably coupled to IDU 110 by a sterile interface module 112 of surgical assembly 100.

The surgical system 1 further includes a control device 4 and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art. Each of the robotic arms 2, 3 may be composed of a plurality of members 2a, 2b, 2c, which are connected through joints. Robotic arms 2, 3 may be driven by electric drives (not shown) that are connected to control device 4. Control device 4 (e.g., a computer) may be set up to activate the drives, in particular by means of a computer program, in such a way that robotic arms 2, 3, the attached robotic surgical assembly 100, and thus electromechanical surgical instrument 130 (including an electromechanical end effector (not shown)) execute a desired movement according to a movement defined by means of manual input devices 7, 8. Control device 4 may also be set up in such a way that it regulates the movement of robotic arms 2, 3.

Robotic surgical system 1 is configured for use on a patient "P" lying on a surgical table "ST" to be treated in a minimally invasive manner by means of a surgical instrument, e.g., electromechanical surgical instrument 130. In embodiments, robotic arms 2, 3 may be coupled to robotic arm cart 10 (FIG. 2) rather than surgical table "ST." Robotic surgical system 1 may also include more than two robotic arms 2, 3, the additional robotic arms likewise being connected to control device 4 and being telemanipulatable by means of operating console 5. A surgical instrument, for example, electromechanical surgical instrument 130 (including the electromechanical end effector), may also be attached to the additional robotic arm.

Figure 13:
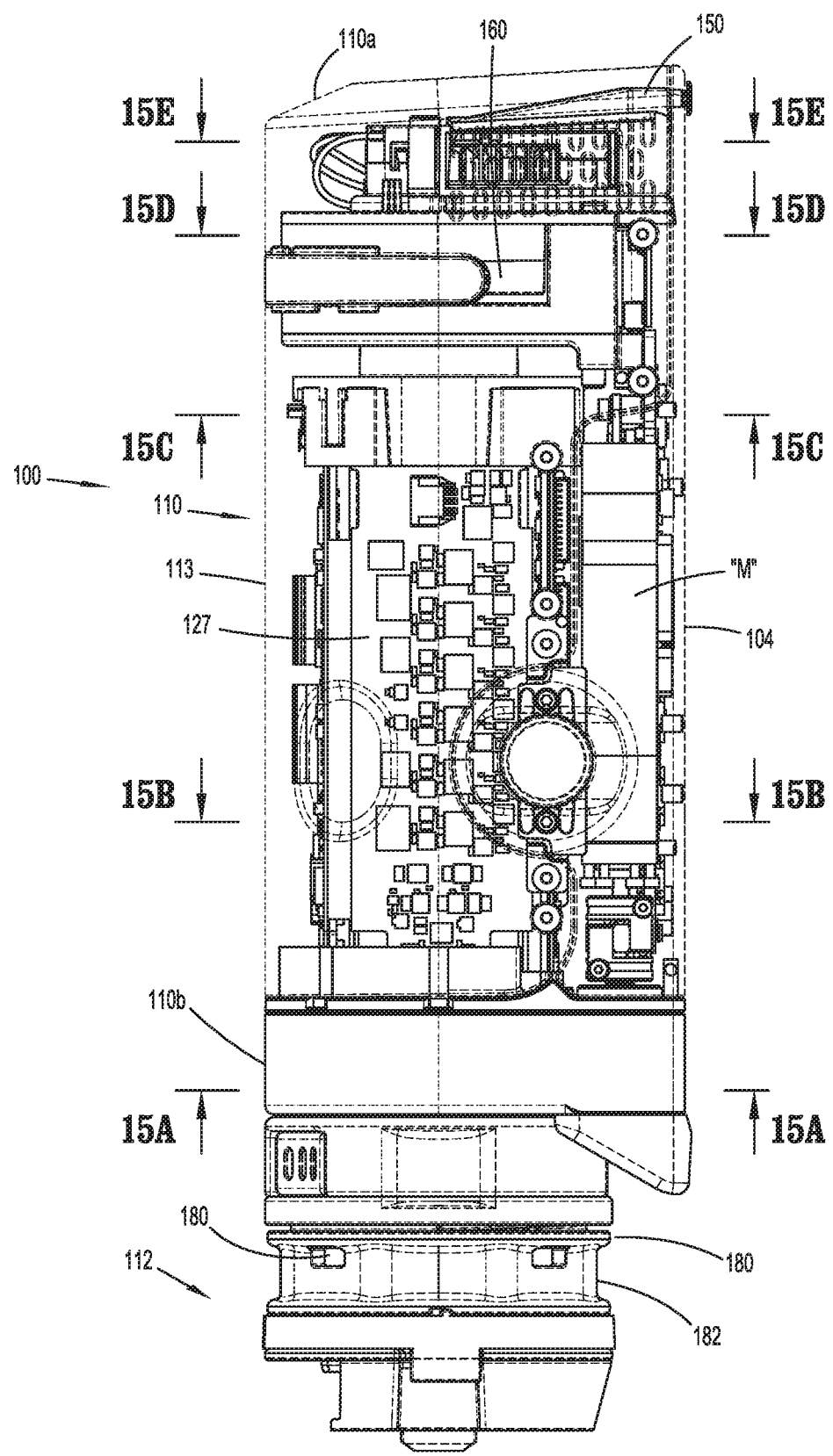
FIG. 13 is a side view of the instrument drive unit coupled with the sterile interface module of FIG. 3.
Figure 14:
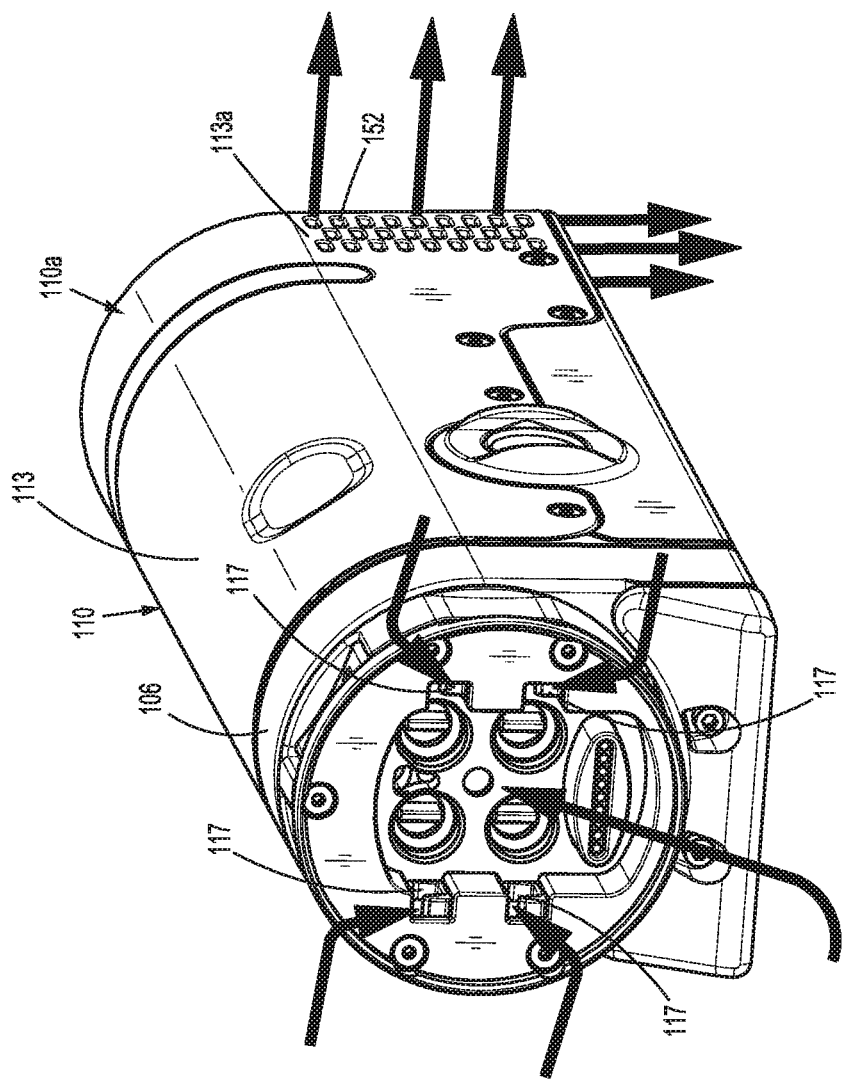
FIG. 14 is a bottom view of the instrument drive unit of FIG. 13.
Figure 15B:
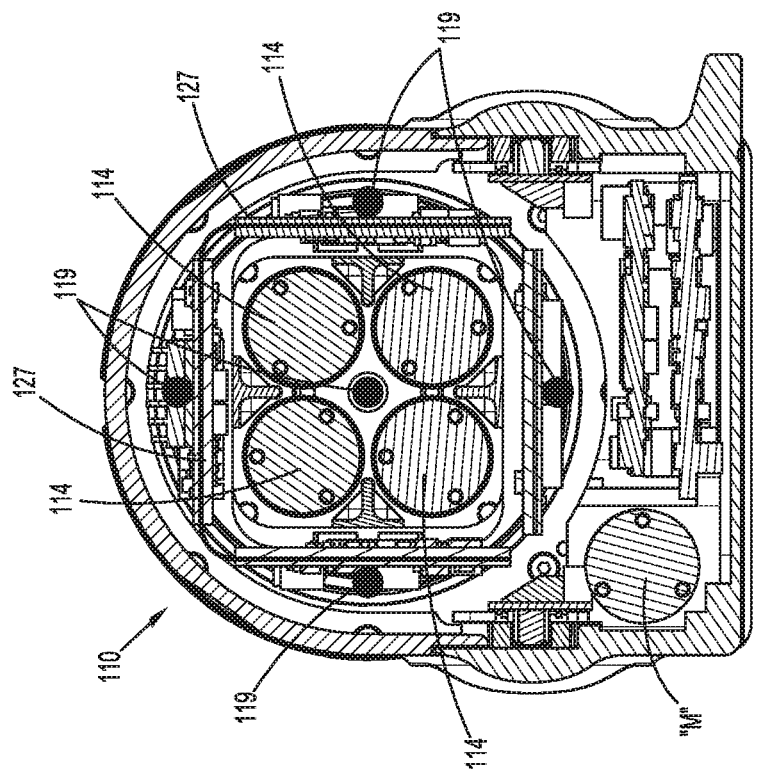
FIG. 15B is a cross-sectional view, taken along line 15B-15B of FIG. 13, illustrating the air channels defined through another portion the instrument drive unit.
Figure 15A:
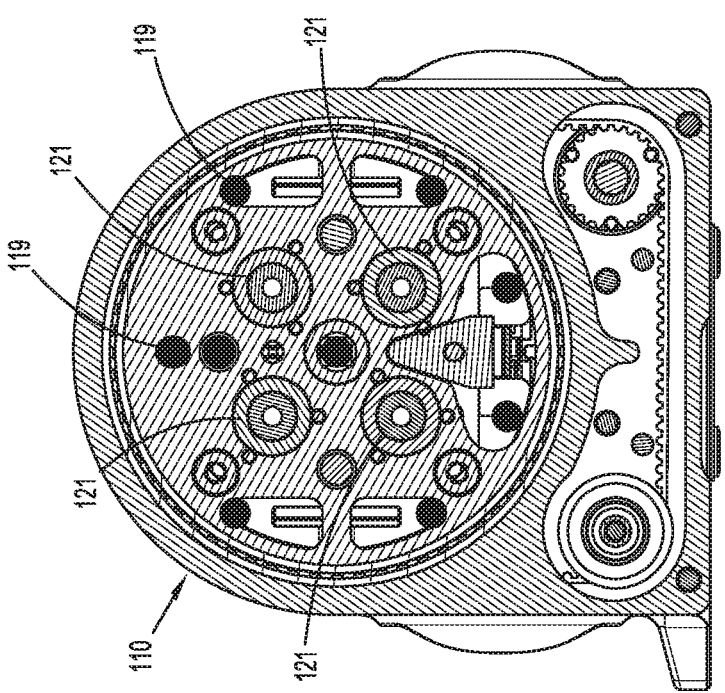
FIG. 15A is a cross-sectional view, taken along line 15A-15A of FIG. 13, illustrating air channels defined through the instrument drive unit.

Control device 4 may control a plurality of motors, e.g., motors (Motor 1 . . . n), with each motor configured to drive movement of robotic arms 2, 3 in a plurality of directions. Further, control device 4 may control a motor assembly 114 (FIG. 7) of IDU 110 of robotic surgical assembly 100 that drives various operations of surgical instrument 130. In addition, control device 4 may control the operation of a rotation motor, such as, for example, a canister motor "M" (FIG. 13) of IDU 110 of surgical assembly 100, configured to drive a relative rotation of motor assembly 114 of IDU 110 and in turn electromechanical surgical instrument 130. In embodiments, each motor 114 of the IDU 110 can be configured to actuate a drive rod/cable or a lever arm to effect operation and/or movement of electromechanical surgical instrument 130.

For a detailed discussion of the construction and operation of a robotic surgical system, reference may be made to U.S. Pat. No. 8,828,023, entitled "Medical Workstation," the entire contents of which are incorporated by reference herein.

With reference to FIGS. 4A-7, drape 200 of robotic surgical system 1 has a generally elongated configuration, such as, for example, a tubular shape, and is fabricated from a resilient material, such as, for example, a natural and/or synthetic fabric or layered material that is impermeable to liquids/moisture. Drape 200 may in embodiments be a single layer or a laminate or fabric, and may be made, e.g., of a nonwoven spun bonded olefin fiber material known as TYVEK®, which is vapor/gas permeable, liquid-resistive, and prevents liquids or contaminants from passing therethrough. In other embodiments, drape 200 may be made of low-density polyethylene (LDPE), high-density polyethylene (HDPE), polypropylene, polyurethane, and/or polyethylene materials or other similar non-toxic, biocompatible compounds. In some embodiments, only some portions of drape 200 may be fabricated from liquid resistant, air-permeable material and at various locations of drape 200. Drape 200 may be translucent so that the components of surgical assembly 100 that drape 200 covers remain visible to a clinician. It is contemplated that drape 200 may be opaque rather than translucent or opaque and translucent along varying portions. Drape 200 has a first end portion or distal end portion 200a, a second end portion or proximal end portion 200b, and an intermediate portion 200c extending between the first and second end portions 200a, 200b. In some embodiments, a high density polyethylene spun woven fiber or synthetic fabric may be glued, thermally bonded, ultrasonically welded, stitched, hook and loop fastened, or seam bonded onto drape 200.

The drape 200 may have any suitable length to cover various portions of the surgical system 1. For example, as shown in FIG. 4A, drape 200 may have a sufficient length to at least allow for second end portion 200b of drape 100 to fit over a base or proximal portion 42 of surgical robotic arm 2. As shown in FIG. 4B, drape 200 may have a sufficient length to at least allow for second end portion 200b to fit over a handle portion 12 of robotic arm cart 10 and be secured to a post 14 of robotic arm cart 10. As shown in FIG. 4C, drape 200 may have a sufficient length to at least allow for second end portion 200b thereof to fit over a base 16 of cart 10. Drape 200 may have a length to accommodate robotic arm 2 in a fully extended position.

Figure 6:
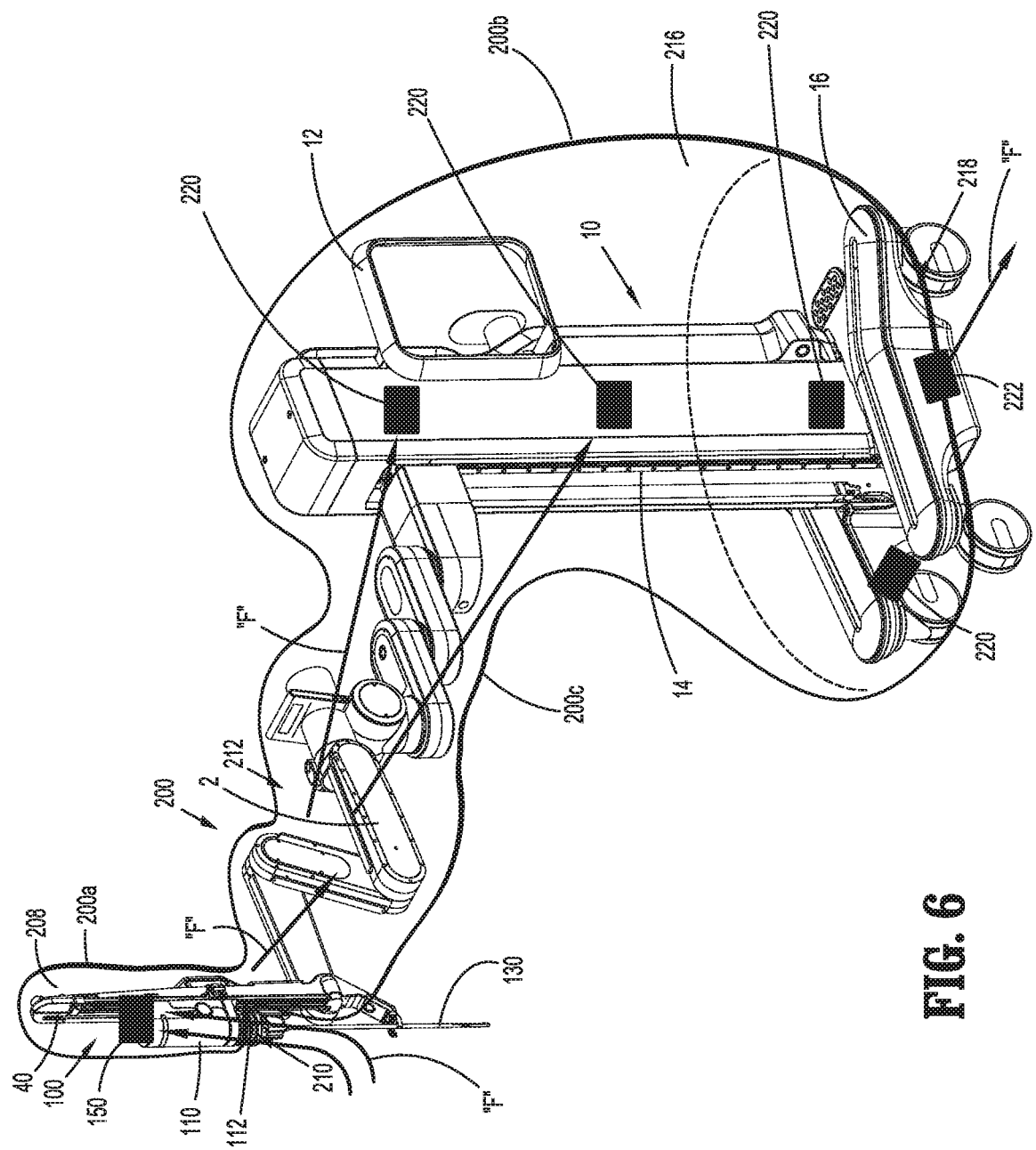
FIG. 6 is a perspective view of the drape of FIG. 5 illustrating a plurality of vents formed in the drape.
Figure 7:
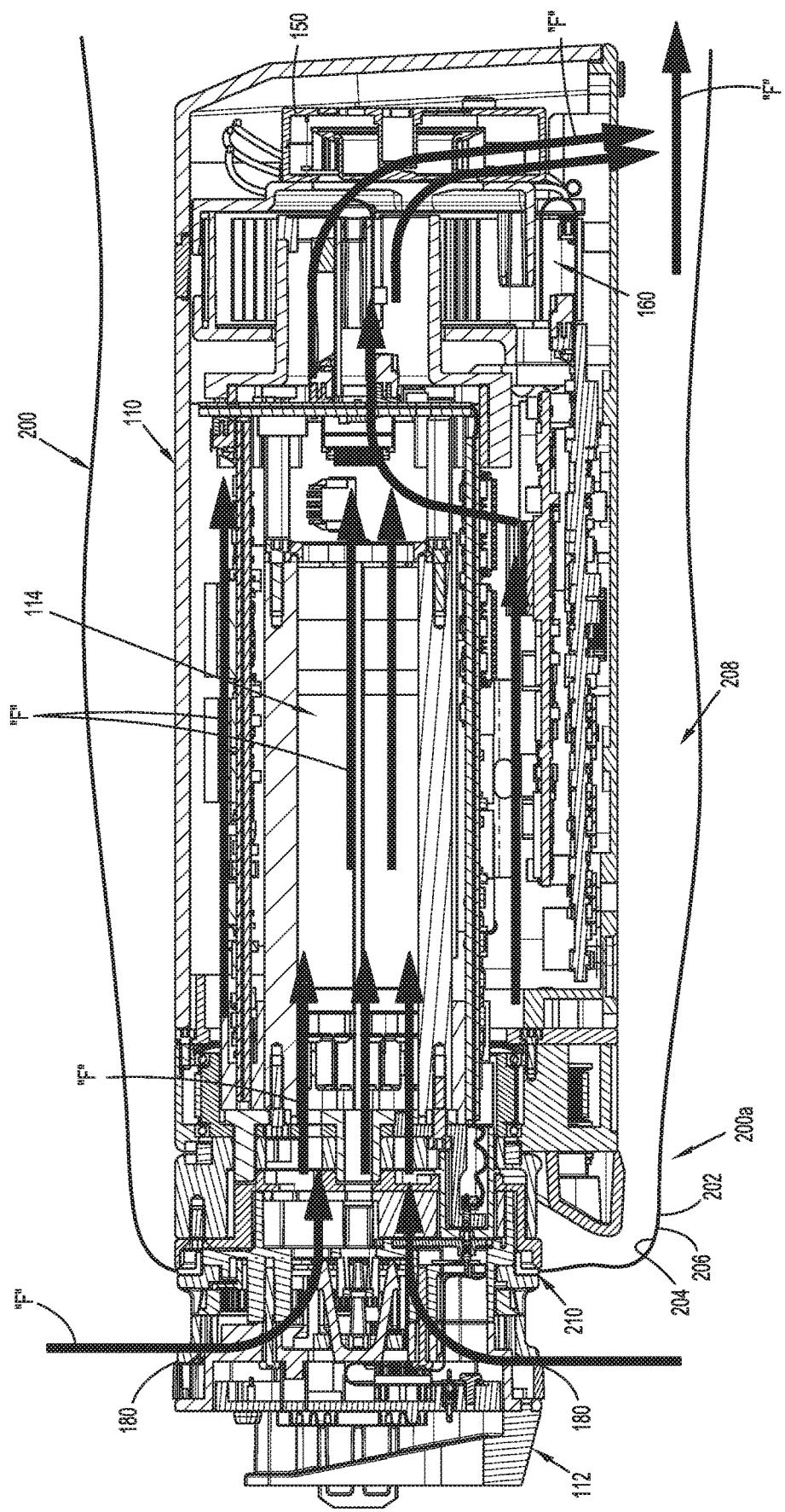
FIG. 7 is a cross-sectional view, taken along line 7-7 of FIG. 3, illustrating an instrument drive unit of the robotic surgical assembly covered by the drape.

With reference to FIGS. 5-7, drape 200 of surgical system 1 is defined by a drape wall 206 having an outer surface 202 and an inner surface 204. Drape wall 206 may be fabricated from the same or a single material and be monolithically formed, or, in some embodiments, drape wall 206 may be fabricated from layers of different materials or from the same material having different properties. The inner surface 204 of drape 200 at the first end portion 200a thereof defines a cavity 208 therein. Cavity 208 of first end portion 200a is dimensioned to receive or encapsulate surgical assembly 100 (e.g., instrument drive unit 110 and slide rail 40).

With continued reference to FIGS. 5-7, first end portion 200a of drape 200 defines an inlet or channel 210 extending through the outer surface 202 and the inner surface 204 of drape 200. Inlet 210 is in fluid communication with cavity 208 of first end portion 200a. As such, inlet 210 provides ingress of air flow "F" into drape 200 to cool components of surgical assembly 100. Inlet 210 has a generally circular or annular shape dimensioned to form a fluid-tight seal with sterile interface module 112 of surgical assembly 100. In some embodiments, inlet 210 may be dimensioned to form a fluid tight seal with a distal end portion 110b (FIG. 3) of instrument drive unit 210 when sterile interface module 112 is not used. During assembly, drape 200 is placed over rail 40 and instrument drive unit 110, and sterile interface module 112 is positioned to extend through inlet 210 of drape 200 with surgical instrument 130 protruding from outer surface 202 of drape 200. Inlet 210 of drape 200 includes a ring (not shown) configured to couple sterile interface module 112 thereto while allowing sterile interface module 112 to rotate relative to and within inlet 210 of drape 200. Air flow "F" travels through dedicated openings 180 defined in sterile interface module 112 and infiltrates first end portion 200a of drape 200. As will be described with reference to FIGS. 8-12, instead of drape 200 having only one inlet 210, drape 200 may have two inlets at first end portion 200a, as will be described.

With continued reference to FIGS. 5-7, intermediate portion 200c of drape 200 is dimensioned to encapsulate or house elongate members 2a, 2b, 2c of surgical robotic arm 2. In particular, intermediate portion 200c of drape 200 defines an elongated conduit 212 extending longitudinally therethrough and dimensioned for receipt of a surgical robotic arm, for example, robotic arm 2. Conduit 212 of intermediate portion 200c has a length dimensioned to accommodate robotic arm 2. In embodiments, the length of conduit 212 is dimensioned to accommodate at least an entire length of robotic arm 2 when robotic arm 2 has each of its elongate members 2a, 2b, 2c in an extended state. Intermediate portion 200c of drape 200 may be fabricated from the same materials as first end portion 200a thereof. In some embodiments, intermediate portion 200c of drape 200 may be fabricated from a different material, or the same material having a different flexibility, as compared to first end portion 200a.

Intermediate portion 200c of drape 200 may have an elongated conductive rib or fin 214 (FIG. 5) attached to and extending from inner surface 204 of drape 200. Fin 214 may be constructed of a thermally-conductive material, such as, for example, woven metals, graphite, copper, or aluminum. Fin 214 may act as a heat sink to facilitate passing heat away from first end portion 200a of drape 200 towards second end portion 200b of drape 200. In some embodiments, fin 214 may be a thermoelectric cooling module for applying active cooling to the air passing thereby. It is contemplated that thermoelectric cooling modules may be positioned at various locations throughout drape 200.

Second end portion 200b of drape 200 defines a cavity 216 therein. Cavity 216 of second end portion 200b is dimensioned to receive or encapsulate at least proximal portion 42 of robotic arm 2 and/or a portion or portions of robotic arm cart 10. Second end portion 200b of drape 200 has an outlet or channel 218 extending through the drape wall 206 of drape 200. As such, outlet 218 of second end portion 200b of drape 200 is in fluid communication with cavity 216 of second end portion 200b of drape 200. Outlet 218 of drape 200 has a generally circular or annular shape that is dimensioned to fit over handle portion of cart 10 and/or cart 10, in embodiments over the entirety of handle portion of cart 10. Outlet 218 of second end portion 200b of drape 200 may be located at a proximal-most end of drape 200 rather than a side of drape 200 as is inlet 210 of first end portion 200a. As such, drape 200 is open at its proximal-most end, whereas drape 200 is closed at its distal-most end. It is contemplated that outlet 218 may be located anywhere along a length of drape 200.

It is contemplated that outlet 218 of drape 200 may include an adhesive lining (not shown) disposed/formed on an inner periphery thereof (e.g., on inner surface 204 of drape 200) for fixing second end portion 200b of drape 200 to cart 10. In an embodiment, outlet 218 of drape 200 may include an elastic band (not explicitly shown), a hook and loop fastener, cinch line, bungee hooks, magnetic material, or the like, surrounding a periphery of second end portion 200b to assist in securing cart 10 within outlet 218 of second end portion 200b. In some embodiments, instead of outlet 218 having an elastic band, outlet 218 may have a tie cord (not explicitly shown) disposed about the periphery of outlet 218 to allow for the diameter of outlet 218 to be adjusted to fit over and secure to various portions of cart 10.

With reference to FIG. 6, second end portion 200b of drape 200 may include one or more pressure-sensitive vents 220 disposed in drape wall 206 of drape 200. Vents 220 are configured to open upon cavity 216 of second end portion 200b of drape 200 achieving a threshold amount of air pressure therein. In this way, if outlet 218 of drape 200 is closed or secured tightly against cart 10 or the like, causing air pressure to build up within second end portion 200b, vents 220 may passively open or may be configured to allow for a continuous passage of air from first end portion 200a, through intermediate portion 200c, and out of second end portion 200b of drape 200 via vents 220. In some embodiments, vents 220 may be in communication with control device 4 (FIG. 1), which may be configured to move vents 220, via a servomechanism or hydraulic drive system for example, between open and closed states based on a temperature or pressure within first end portion 200a, intermediate portion 200c, and/or second end portion 200b of drape 200. It is contemplated that control device 4 may be configured to move vents 220 between the opened and closed states based on a speed of fan 150 of IDU 110. It is contemplated that vents 220 may be configured to remain open to act as inlets rather than outlets. Vents 220 may be fabricated from a liquid-resistant, air-permeable material (e.g., polyethylene fibers or polypropylene) which permits passive passage of air flow therethrough. In one embodiment, vents 220 may be coupled to drape wall 206 of drape 200 using a piece of shape memory material (e.g., a shape memory alloy) configured to expand upon achieving a threshold temperature. As such, the shape memory material lifts or raises vent 220 relative to drape wall 206, thereby creating an opening in drape wall 206 for air to pass through.

Second end portion 200b may also include a fan (not shown) that draws air from first end portion 200a toward outlet 218 of second end portion 200b of drape 200. In some embodiments, cart 10 may include fans 222, 224 attached to base 16 and/or handle portion 12 of cart 10, respectively. Fans 222, 224 of cart 10 may draw air from first end portion 200a of drape 200 toward outlet 218 of second end portion 200b of drape 200.

During assembly or application of drape 200 to cart 10, second end portion 200b of drape 200 is placed over handle portion 12 of cart 10 and secured to the post 14 of cart 10, as shown in FIG. 5. In some embodiments, during assembly, second end portion 200b of drape 200 may cover handle portion 12, post 14, and base 16 of cart 10 and be secured to an under-surface of base 16 of cart 10 as shown in FIG. 6. While second end portion 200b of drape 200 is secured to cart 10, outlet 218 of second end portion 200b of drape 200 remains open to allow for air flow "F" to pass through.

The fan 150 of IDU 110 is activated to generate negative pressure within cavity 208 of first end portion 200a, which draws the air flow "F" into drape 200 through sterile interface module 112, from the sterile field. Air flow "F" continues to travel through the IDU 110 to cool components of the IDU 110. The air flow "F" then travels out of the IDU 110 through the fan 150 and through the first end portion 200a, the intermediate portion 200c, and then the second end portion 200b of drape 200. The air flow "F," now warmed by absorbing heat generated from the operation of IDU 110, will ultimately move out of drape 200 via outlet 218 and/or vents 220 and into the operating room or non-sterile field.

Figure 8:
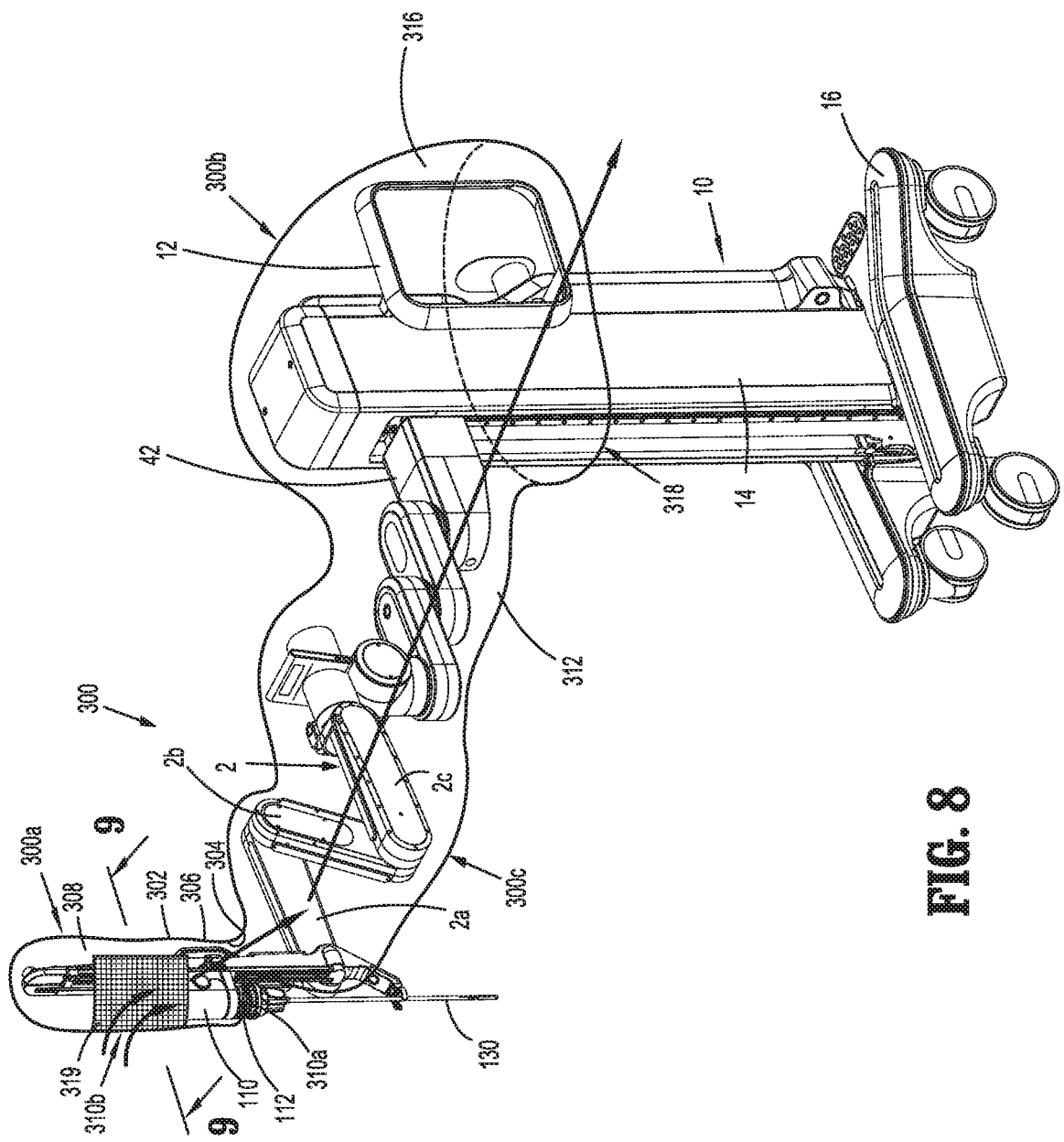
FIG. 8 is a perspective view of the robotic surgical assembly, the robotic arm, and the robotic arm cart shown in FIG. 2 each covered by another embodiment of a drape.
Figure 9:
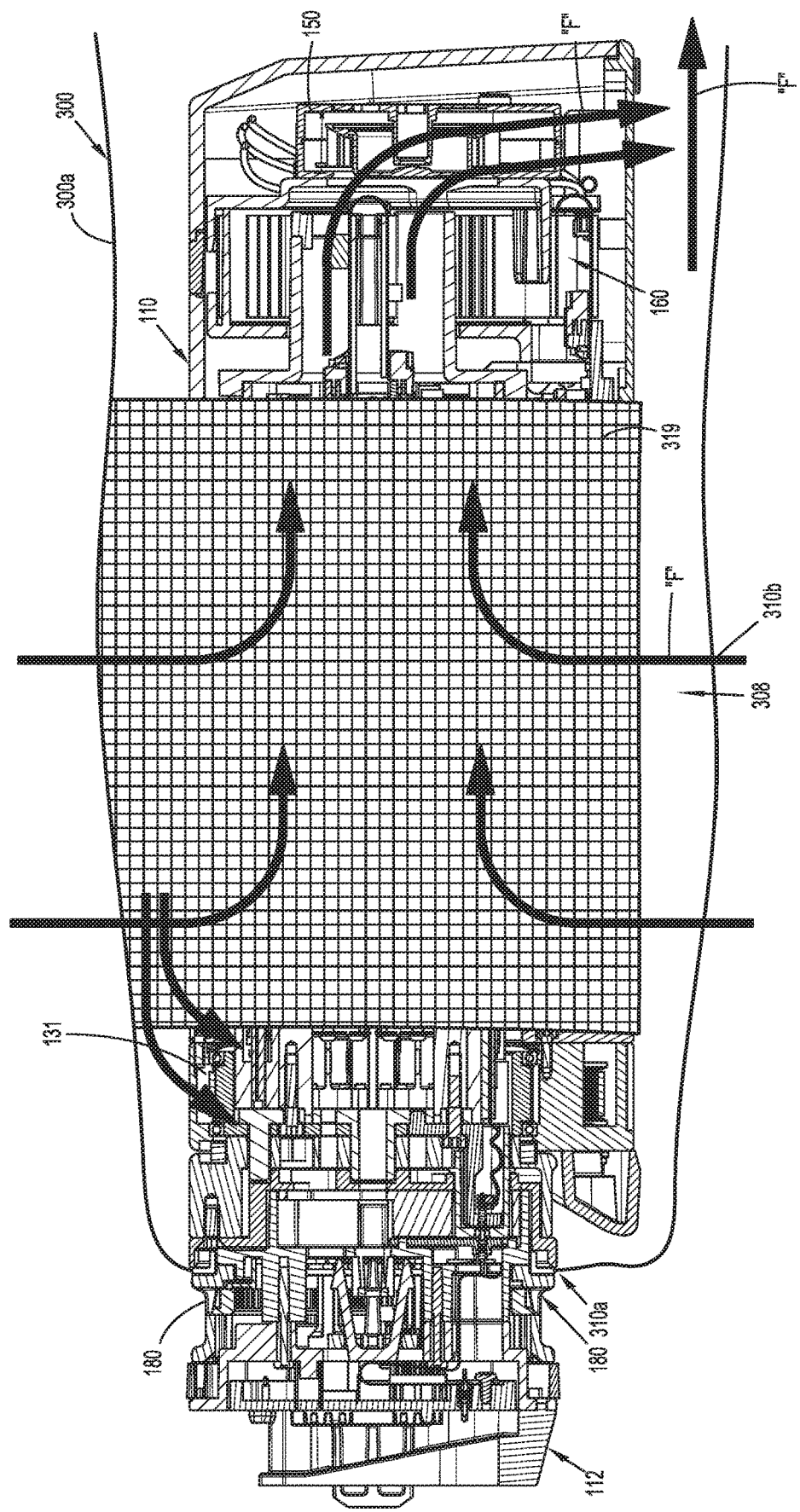
FIG. 9 is a cross-sectional view, taken along line 7-7 of FIG. 3, illustrating the instrument drive unit of the robotic surgical assembly covered by the drape of FIG. 8.

With reference to FIGS. 8 and 9, another embodiment of a drape 300 for covering surgical assembly 100, surgical robotic arm 2, and portions of robotic arm cart 10, is provided. Drape 300 includes a drape wall 306 having an outer surface 302 and an inner surface 304. Outer surface 302 and inner surface 304 of drape wall 306 are each fabricated from the same material, and are monolithically formed with one another. In some embodiments, one or each of the outer surface 302 and the inner surface 304 of drape wall 306 of drape 300 may be fabricated from different layers of materials or the same material having different properties. The inner surface 304 at a first end portion 300a of drape 300 defines a cavity 308 therein. Cavity 308 of first end portion 300a of drape 300 is dimensioned to receive or encapsulate surgical assembly 100 (e.g., instrument drive unit 110 and slide rail 40).

Instead of first end portion 300a of drape 300 only having one inlet as is the case in first end portion 200a of drape 200 described above with reference to FIGS. 5-7, first end portion 300a of drape 300 of the present embodiment defines at least two inlets 310a, 310b each extending through the drape wall 306 of drape 300. As such, first and second inlets 310a, 310b are each in fluid communication with cavity 308 of first end portion 300a. First inlet 310a of drape 300, similar to inlet 210 of drape 200, has a generally circular or annular shape dimensioned to form a seal with a sterile interface module 112 of surgical assembly 100. In some embodiments, first inlet 310a may be dimensioned to form a seal with the bottom portion 110b (FIG. 3) of instrument drive unit 110 rather than sterile interface module 112.

In use, drape 300 is placed over surgical assembly 100, and sterile interface module 112 is positioned to extend through first inlet 310a with surgical instrument 130 protruding from drape 300.

Second inlet 310b of first end portion 300a of drape 300 is disposed distally of first inlet 310a (i.e., further away from second end portion 300b of drape 300). Second inlet 310b is positioned at a location of first end portion 300a of drape 300 that lies adjacent a side portion of instrument drive unit 110 when drape 300 is positioned over surgical assembly 100, as shown in FIG. 8. Second inlet 310b of drape 300 may be covered with an air-breathable patch 319 that prohibits liquids/moisture from passing into cavity 308 of first end portion 300a while permitting ingress of air through the second inlet 310b. For example, patch 319 may be made of a nonwoven spun bonded olefin fiber material commonly known as TYVEK®. Patch 319 may be made of any suitable organic, natural, and/or synthetic single layer or multi-layered material including parylene, HDPE, PTFE, polymer coated water proof vapor/gas permeable fabric, flashspun high-density polyethylene fibers, woven or non-woven fabric, a porous-polymer, or any combination thereof. In this way, patch 319 prohibits liquids from entering the interior of drape 300 while allowing air to enter cavity 308 of first end portion 300a of drape 300, which then passes through instrument drive unit 110 to cool the internal components of instrument drive unit 110.

With continued reference to FIGS. 8 and 9, intermediate portion 300c of drape 300 is dimensioned to encapsulate or house elongate members 2a, 2b, 2c of surgical robotic arm 2. In particular, intermediate portion 300c of drape 300 defines an elongated conduit 312 extending longitudinally therethrough and dimensioned for receipt of a surgical robotic arm, for example, robotic arm 2. Conduit 312 of intermediate portion 300c has a length dimensioned to accommodate robotic arm 2, in embodiments to accommodate at least an entire length of robotic arm 2 when robotic arm 2 has each of its elongate members 2a, 2b, 2c in an extended state. Intermediate portion 300c of drape 300 may be fabricated from the same elastomeric materials as first end portion 300a. In some embodiments, intermediate portion 300c of drape 300 may be fabricated from a different material, or the same material having a different flexibility, as compared to first end portion 300a.

Intermediate portion 300c may have an elongated conductive rib or fin (not explicitly shown), similar to fin 214 of drape 200, attached to inner surface 304 of drape 300. The fin of drape 300 may act as a heat sink to facilitate passing heat away from first end portion 300a of drape 300 towards second end portion 300b of drape 300.

Second end portion 300b of drape 300 defines a cavity 316 therein. Cavity 316 of second end portion 300b is dimensioned to receive or encapsulate at least proximal portion 42 of robotic arm 2 and/or a portion or portions of robotic cart 10. Second end portion 300b of drape 300 has an outlet 318 extending through drape wall 306 of drape 300. As such, outlet 318 of second end portion 300b is in fluid communication with cavity 316 of second end portion 300b of drape 300. Outlet 318 of drape 300 has a generally circular or annular shape dimensioned to fit over handle portion 12 of cart 10 or cart 10 in its entirety. Outlet 318 of second end portion 300b of drape 300 may be located at a proximal-most end of drape 300 rather than a side of drape 300 as is first and second inlets 310a, 310b of first end portion 300a. As such, drape 300 is open at its proximal-most end, whereas drape 300 is closed at its distal-most end.

In use, drape 300 is positioned over surgical assembly 100, robotic arm 2, and handle portion 12 of cart 10, as shown in FIG. 8. Sterile interface module 112 extends through first inlet 310a of drape 300 such that an upper portion of sterile interface module 112 resides within cavity 308 of first end portion 300a and a bottom portion of sterile interface module 112 is disposed outside of drape 300. The second inlet 310b of drape 300 is disposed adjacent a side portion of instrument drive unit 110 to align with openings 131 defined in instrument drive unit 110. Air flow "F," generated by, for example, fan 150, moves through second inlet 310b of drape 300 and into the cavity 308 of drape 300. In particular, as air flow "F" moves through second inlet 310b of drape 300, it passes into cavity 308 via patch 319 such that substantially all of the moisture moving with air flow "F" is captured by patch 319 without entering cavity 308 of drape 300. The air flow "F" then travels into IDU 110 via openings 131 defined in IDU 110 and exits the IDU 110 via fan 150 to cool the internal components of IDU 110. The air flow "F," now having absorbed heat generated by the working components of IDU 110, moves through conduit 312 of intermediate portion 300c of drape 300 and out of second end portion 300b of drape via outlet 318. In some embodiments, air travels into drape 300 via both first and second inlets 310a, 310b and not just second inlet 310b.

Figure 10:
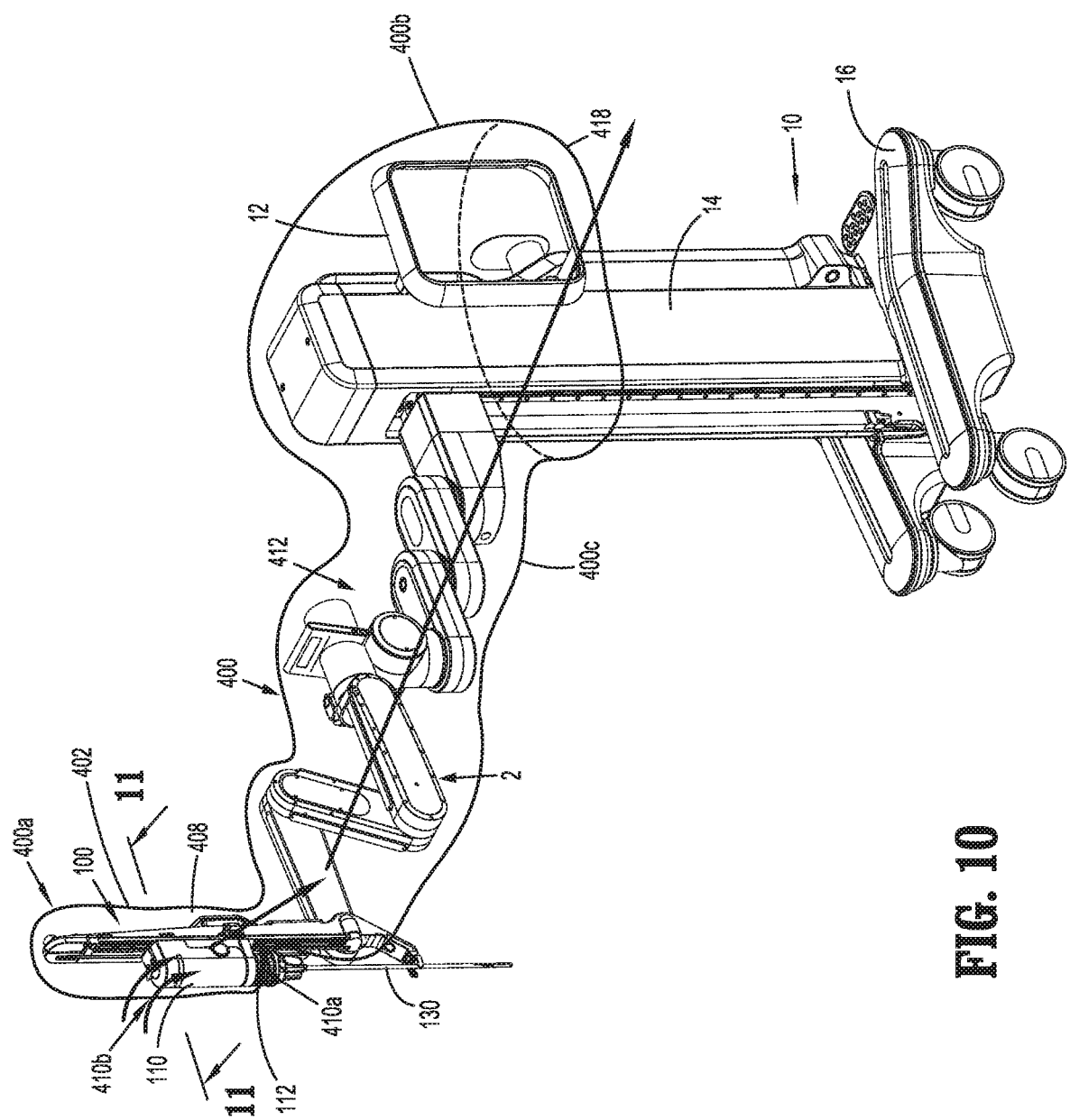
FIG. 10 is a perspective view of the robotic surgical assembly, the robotic arm, and the robotic arm cart shown in FIG. 2 each covered by another embodiment of a drape.
Figure 11:
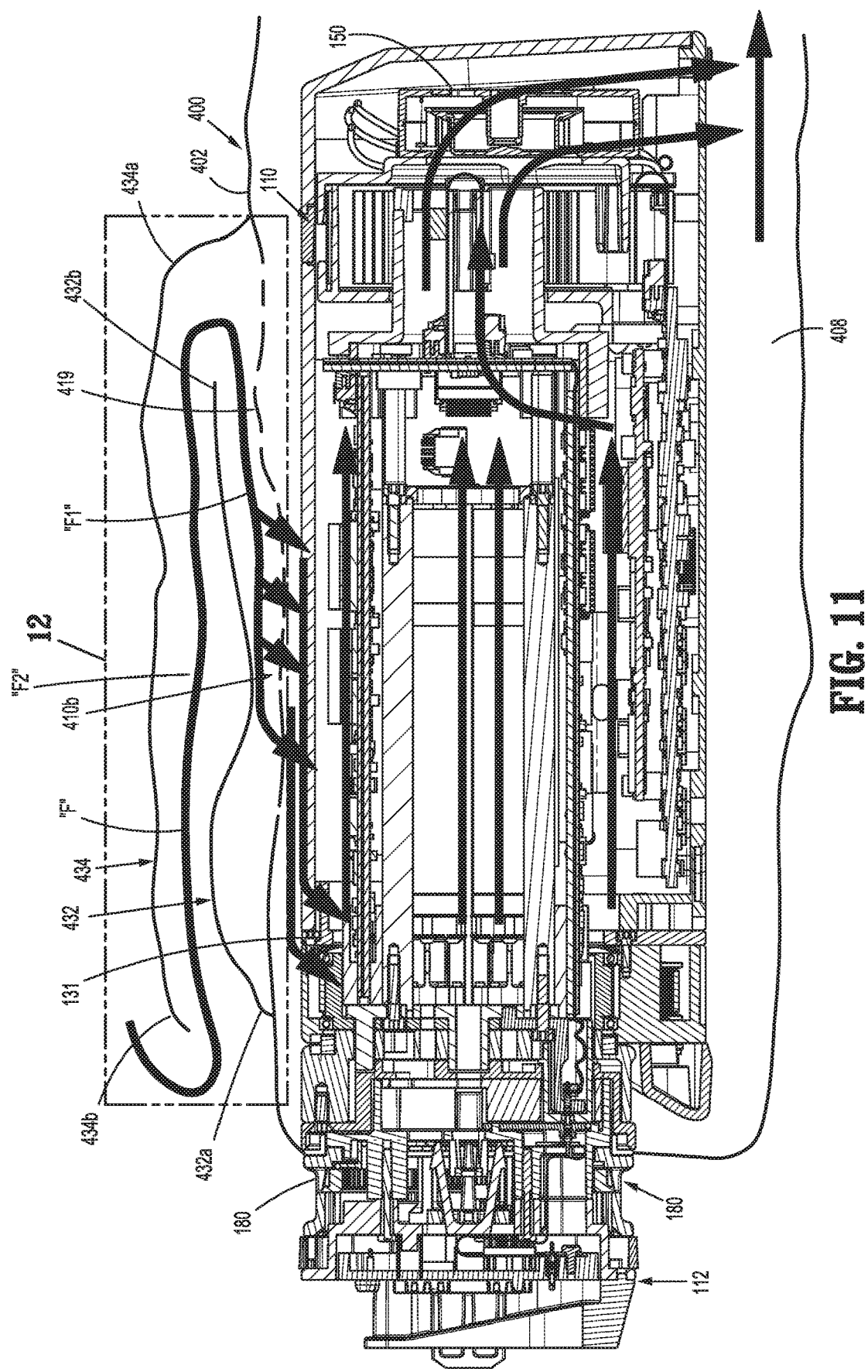
FIG. 11 is a cross-sectional view, taken along line 7-7 of FIG. 3, illustrating the instrument drive unit of the robotic surgical assembly covered by the drape of FIG. 10.
Figure 12:
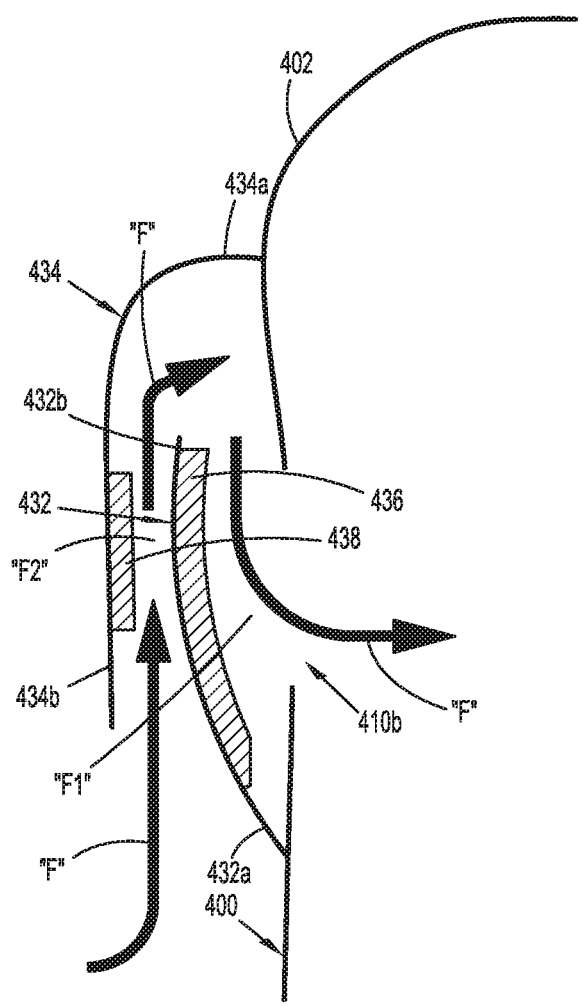
FIG. 12 is an enlarged view of detail 12 of the drape shown in FIG. 11.

With reference to FIGS. 10-12, another embodiment of a drape 400 is shown, similar to drape 300 described with reference to FIGS. 8 and 9. Drape 400 is similar to drape 300 except that in addition to having the patch 319 (FIG. 9), or alternatively to having the patch 319, a first end portion 400a of drape 400 includes first and second overlapping flaps or baffles 432, 434 that cover an inlet 410b. First and second flaps 432, 434 extend from an outer surface 402 of drape 400. First flap 432 is fabricated from a harder, less flexible material than outer surface 402 of drape 400. In some embodiments, first flap 432 may be fabricated from the same air permeable material as drape 400 or a more elastic/flexible material than drape 400. First flap 432 has a first end portion 432a connected to outer surface 402 of drape 400 at a location adjacent a first side of second inlet 410b.

Inlet 410b has a perforated covering or section 419 that allows for air flow "F" to pass therethrough while prohibiting moisture from passing therethrough. In some embodiments, instead of having perforated covering 419, inlet 410b may have a liquid resistant, air-permeable covering or may be covered with patch 319 or be devoid of any covering other than first and second flaps 432, 434.

First flap 432 has a second or free end portion 432b that extends over inlet 410b while being spaced from outer surface 402 to define a first fluid pathway or channel "F1" that is substantially parallel with outer surface 402.

Second flap 434 of drape 400 is similar to first flap 432 and has a first end portion 434a connected to outer surface 402 of drape wall 406 adjacent a second side of second inlet 410b, opposite the first side of second inlet 410b. Second flap 434 has a second or free end portion 434b that extends over second end portion 432b of first flap 432 while being spaced from second end portion 432b of first flap 432 to define a second fluid pathway or channel "F2" that is substantially parallel with first fluid pathway "F1." First and second fluid pathways "F1," "F2" are in fluid communication with one another to allow for air to pass from second fluid pathway "F2," through first fluid pathway "F1," and into cavity 408 of first end portion 400a via second inlet 410b.

With reference to FIG. 12, first end portion 400a of drape 400 may include first and second ribs 436, 438 disposed in, and extending parallel with, respective first and second pathways "F1," "F2" of second inlet 410b. In some embodiments, ribs 436, 438 may extend at any suitable orientation relative to pathways "F1," "F2" of second inlet 410b, such as, perpendicular. First and second ribs 436, 438 each have an elongated configuration and are narrower in width than a width of first and second fluid pathways "F1," "F2" so as to not disrupt air flow through first and second pathways "F1," "F2." First rib 436 is disposed between outer surface 402 of first end portion 400a of drape 400 and first flap 432. Second rib 438 is attached to an inner surface of second flap 434 so as to be disposed between first and second flaps 432, 434. First and second ribs 436, 438 prevent and/or resist fluid pathways "F1," "F2" from collapsing by maintaining spacing between first and second flaps 432, 434, and first flap 432 and outer surface 402 of first end portion 400a of drape 400.

It is contemplated that first and second ribs 436, 438 may be fabricated from a less flexible material than first and second flaps 432, 434.

In some embodiments, instead of using ribs 436, 438 to prevent and/or resist fluid pathways "F1," "F2" from collapsing, first and second pathways "F1," "F2" of second inlet 410b may include a sponge/mesh, open-cell foams, springs, or tubes disposed therein, or opposing magnets disposed on opposite sides of flaps 432, 434.

In use, drape 400 is positioned over surgical assembly 100, robotic arm 2, and handle portion 12 of cart 10, as shown in FIG. 10. Sterile interface module 112 extends through a first inlet 410a of drape 400 such that an upper portion of sterile interface module 112 resides within cavity 408 of first end portion 400a and a bottom portion of sterile interface module 112 is disposed outside of drape 400. The second inlet 410b of drape 400 is disposed adjacent a side portion of instrument drive unit 110 to align with openings 131 defined in instrument drive unit 110. Air flow "F" moves into second fluid pathway "F2" (from the sterile field), then through first fluid pathway "F1," and into cavity 408 of first end portion 400a via second inlet 410b.

As air flow "F" moves through second inlet 410b of drape 400, it passes into IDU 110 via openings 131 defined in IDU 110 and exits the IDU 110 via fan 150 to cool the internal components of IDU 110. In some embodiments, air flow "F" may first travel into IDU 110 via fan 150 and exit through openings 131 of IDU 110 or other openings of IDU 110. The air flow "F," now having absorbed heat generated by the working components of IDU 110, moves through a conduit 312 of intermediate portion 400c of drape 400 and out of a second end portion 400b of drape via an outlet 418 of second end portion 400b and out into the non-sterile field. In some embodiments, air travels into drape 400 via both first and second inlets 410a, 410b and not just second inlet 410b.

With reference to FIGS. 13-20, surgical assembly 100 of surgical system 1, which is configured to be coupled with or to robotic arm 2 or 3 (FIG. 2), generally includes the IDU 110, the sterile interface module 112, and the electromechanical surgical instrument 130 (FIG. 2). As briefly mentioned above, IDU 110 transfers power and actuation forces from its motors 114 to driven members (not shown) of electromechanical surgical instrument 130 to ultimately drive movement of components of the end effector of electromechanical surgical instrument 130, for example, a movement of a knife blade (not shown) and/or a closing and opening of jaw members of the end effector, the actuation or firing of a stapler, and/or the activation or firing of an electrosurgical energy-based instrument, or the like. Motor assembly 114 of IDU 110 is rotated by a motor "M" disposed in IDU 110 and transfers its rotational motion to electromechanical surgical instrument 130.

With reference to FIGS. 13-15E, IDU 110 includes a housing cover 113 coupled to rail 40 of surgical robotic arm 2. Housing cover 113 of IDU 110 enshrouds, covers, and protects the inner components of IDU 110. Housing cover 113 of IDU 110 may have a generally cylindrical configuration, but in some embodiments, housing cover 113 may assume a variety of configurations, such as, for example, square, triangular, elongate, curved, semi-cylindrical or the like. As mentioned above, housing cover 113 protects or shields various components of IDU 110 including motor assembly 114 and a flex spool assembly 160 that transfers power and data to components of IDU 110.

Motor assembly 114 of IDU 110 may include four motors, for example, canister motors or the like, each having a drive shaft 121 configured to interface with corresponding drives

185 (FIG. 17A) of sterile interface module 112. While IDU 110 is illustrated as having four motors, it is contemplated that IDU 110 may include any suitable number of motors. Drive shafts 121 of IDU 110 have non-circular transverse cross-sectional profiles (e.g., substantially D-shaped, or the like). The four motors of motor assembly 114 are arranged in a rectangular formation such that the respective drive shafts 121 thereof are all parallel with one another and all extending in a common direction. As the motors of the motor assembly 114 are actuated, rotation of the respective drive shafts 121 is transferred to gears or couplers of drive assemblies of surgical instrument 130 via respective drive transfer shafts 185 of sterile interface module 112 to actuate various functions of surgical instrument 130.

With reference to FIGS. 14 and 15A-15E, IDU 110 defines a plurality inlets or openings 117 in a bottom portion 110b thereof. Openings 117 of IDU 110 are in fluid communication with corresponding channels 180 (FIG. 17A-17C) defined in sterile interface module 112 such that air passes from sterile interface module 112 into IDU 110 via openings 117 of IDU 110. IDU 110 defines a plurality of channels 119 (FIGS. 15A-15C) extending longitudinally between opposite ends 110a, 110b of IDU 110. In particular, channels 119 are in fluid communication with openings 117 defined in bottom portion 110b of IDU 110 and terminate adjacent a fan 150 of IDU 110 located at a top portion 110a of IDU 110. Channels 119 are disposed between motors of motor assembly 114 to provide passage of air therethrough to cool the motor assembly 114. Channels 119 also extend alongside elongate flex circuit boards 127 of IDU and a nexus 129 of IDU 110 to provide an ingress for heat generated by elongated flex circuit boards 127 and the nexus 129 that connects with elongated flex circuit boards 127. Channels 119 terminate within a central cavity 162 defined in flex spool assembly 160 such that air can pass through central cavity 162 to cool flex spool assembly 160.

Figure 16A:
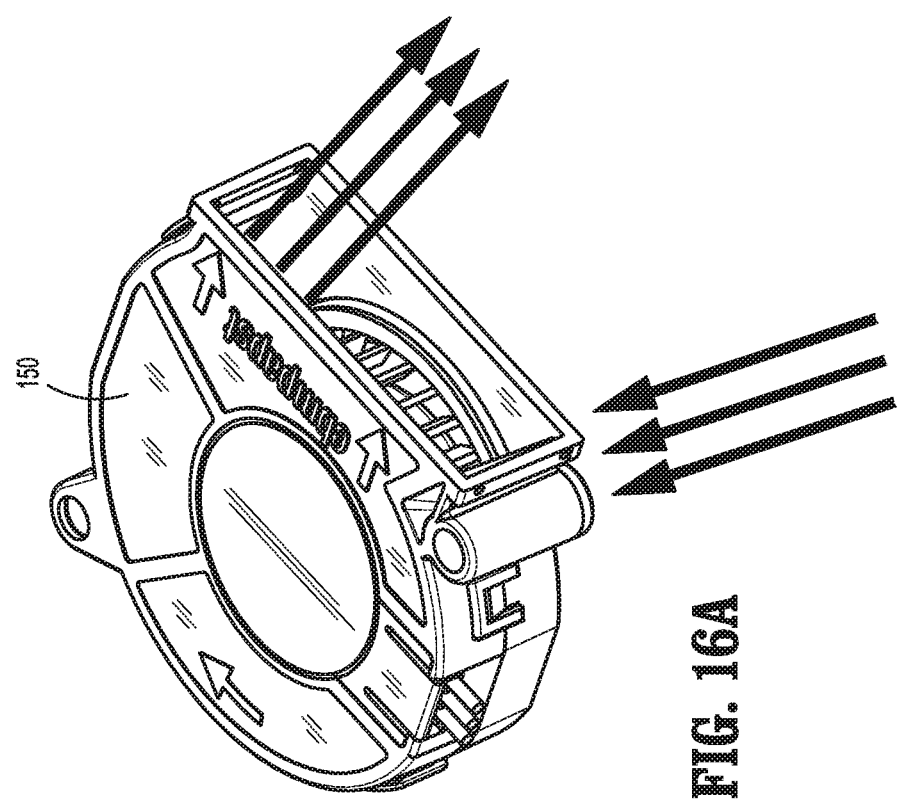
FIG. 16A is a perspective view of a fan of the instrument drive unit of FIG. 3.
Figure 15E:
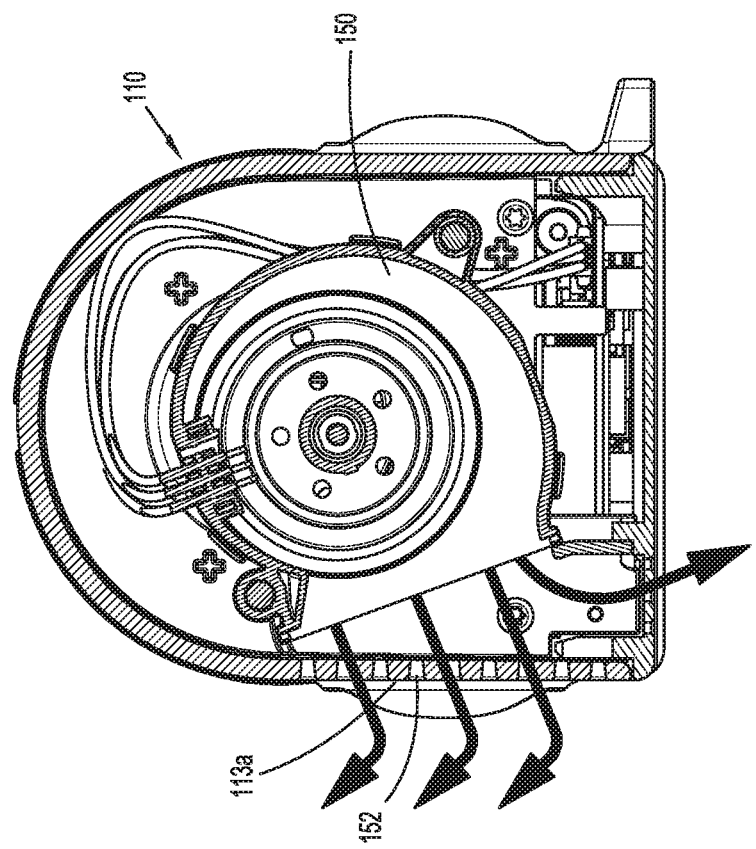
FIG. 15E is a cross-sectional view, taken along line 15E-15E of FIG. 13, illustrating a fan of the instrument drive unit.
Figure 17A:
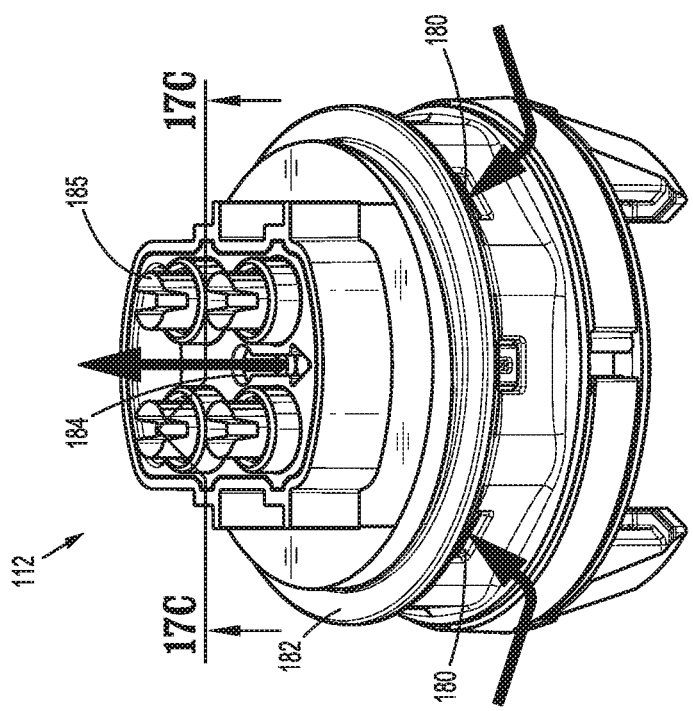
FIG. 17A is a top, perspective view of the sterile interface module of FIG. 3 illustrating air channels defined therein.
Figure 16B:
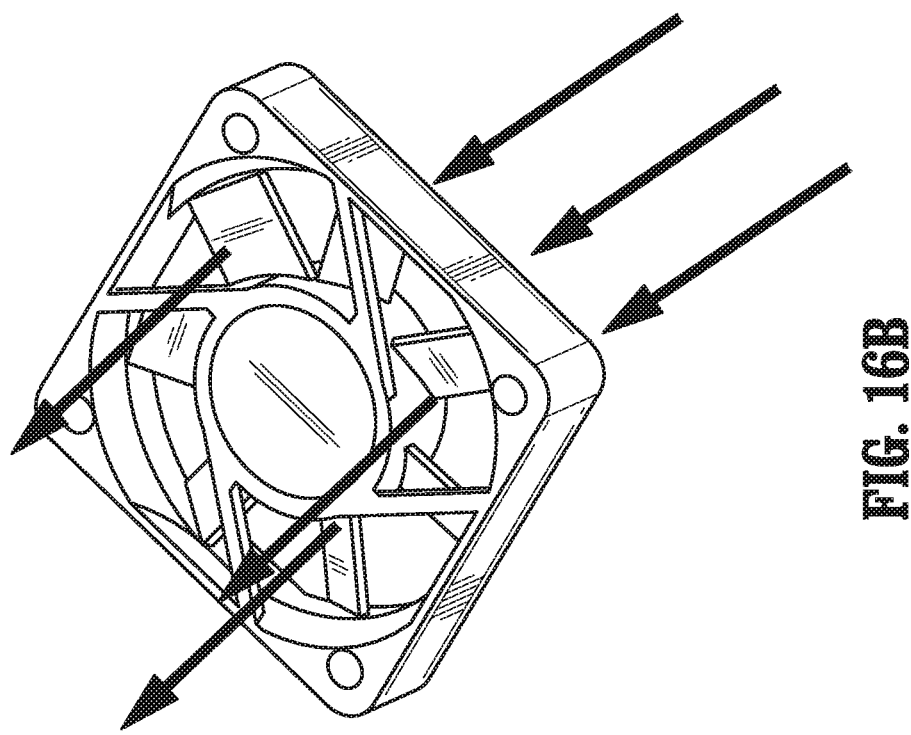
FIG. 16B is a perspective view of another embodiment of a fan of the instrument drive unit of FIG. 3.
Figure 17C:
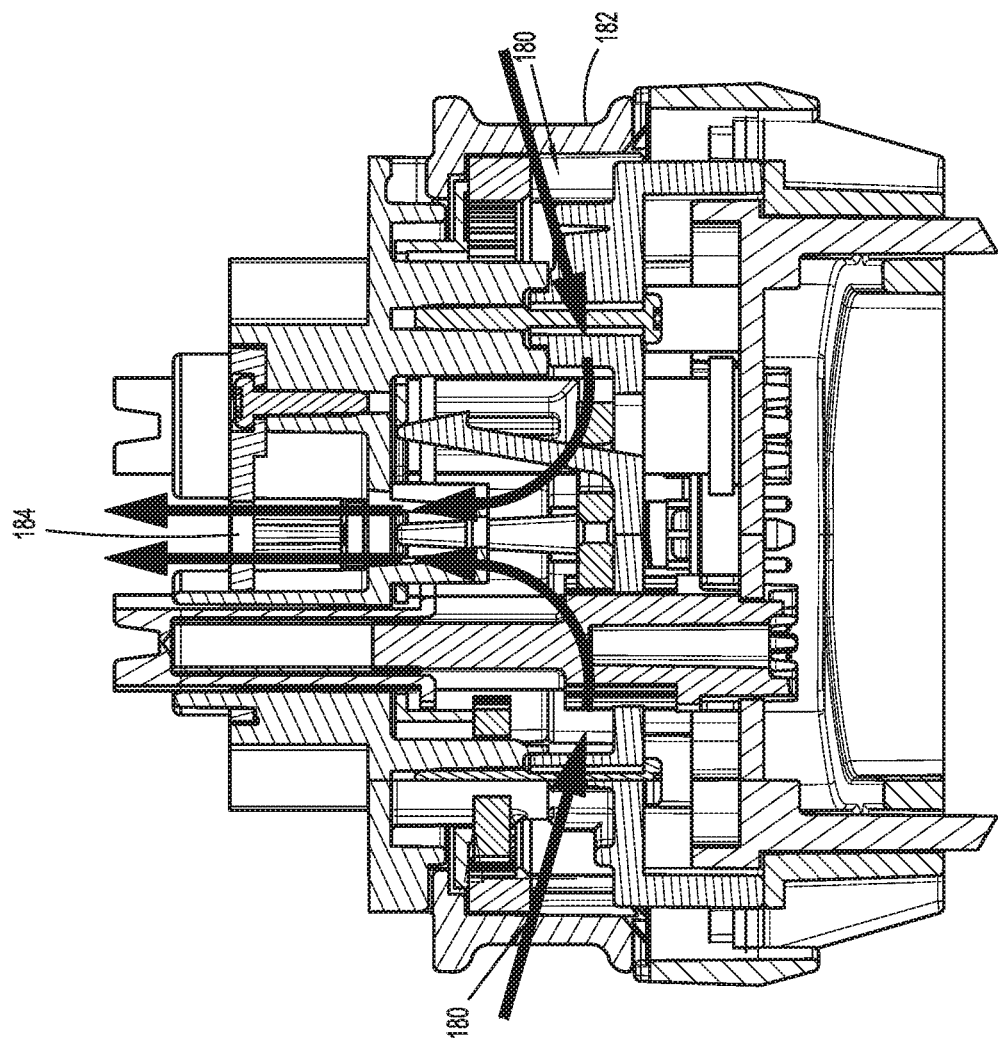
FIG. 17C is a cross-sectional view, taken along line 17C-17C of FIG. 17A, illustrating air channels defined through the sterile interface module.
Figure 17B:
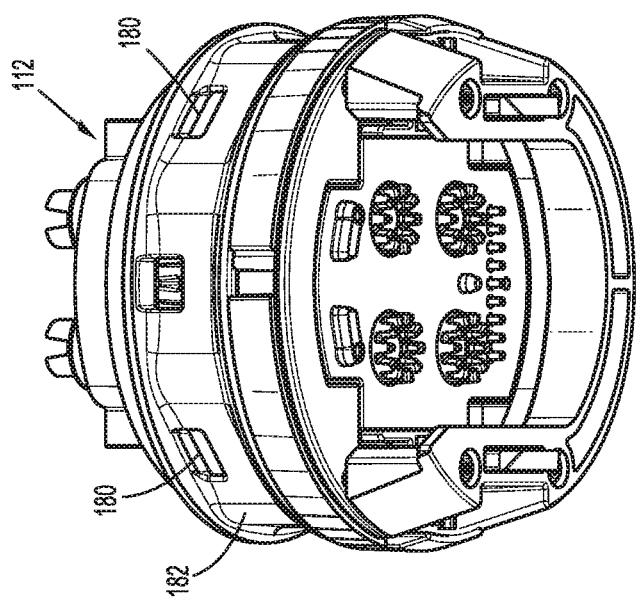
FIG. 17B is a bottom, perspective view of the sterile interface module of FIG. 3.
Figure 19:
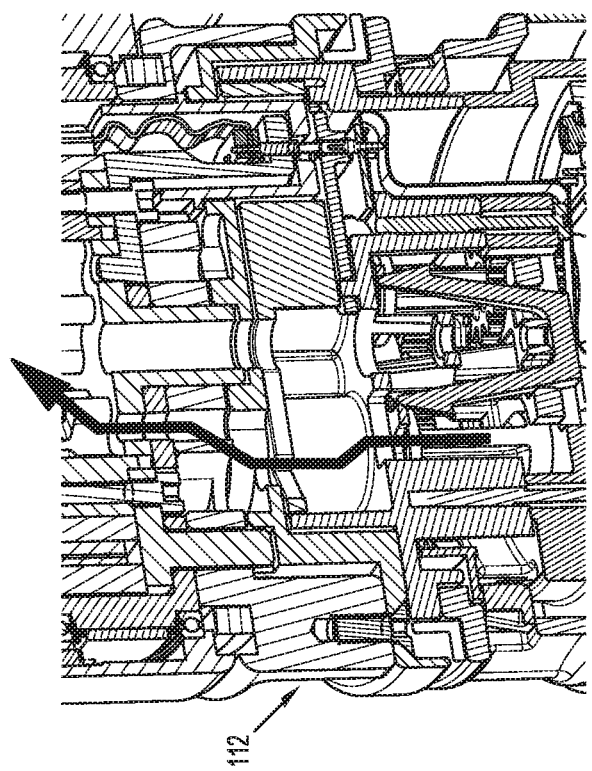
FIG. 19 is an enlarged, cross-sectional view of the sterile interface module of FIG. 17A.
Figure 18:
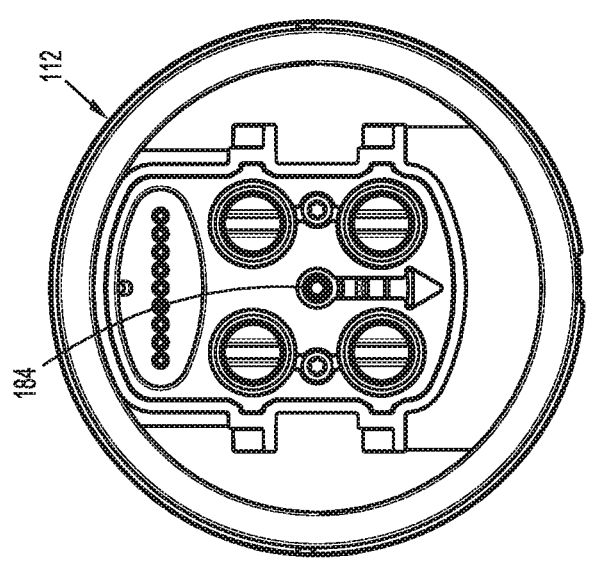
FIG. 18 is a top view of the sterile interface module of FIG. 17A.
Figure 20:
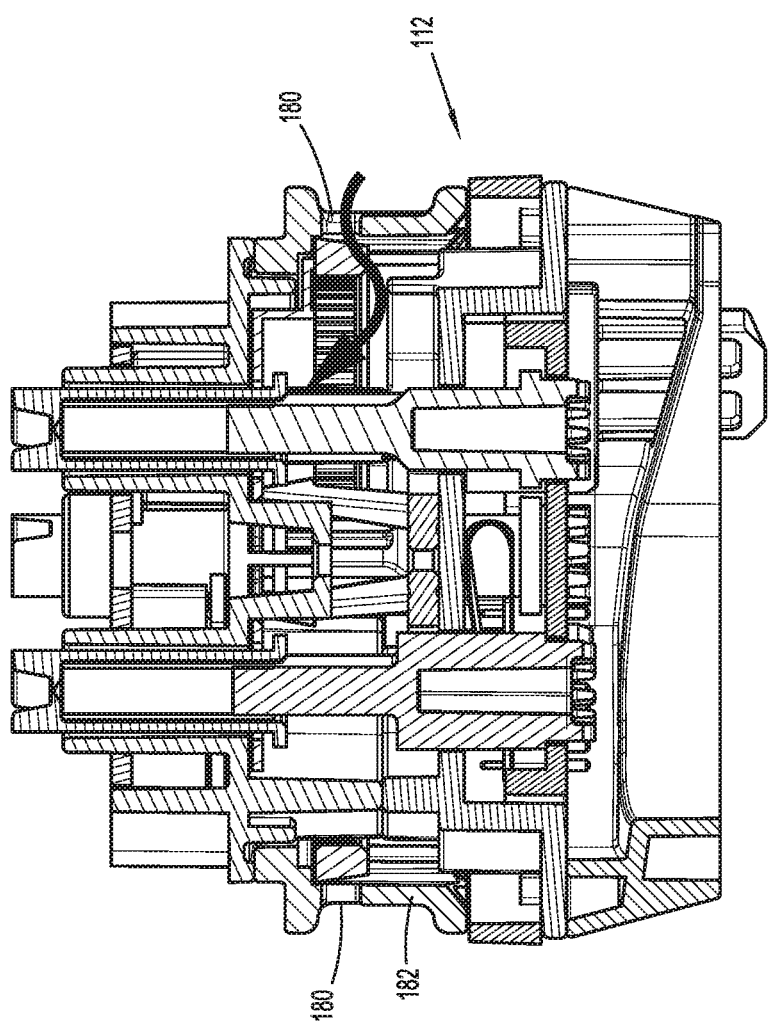
FIG. 20 is another cross-sectional view of the sterile interface module of FIG. 17A.

IDU 110 includes a fan 150 disposed within the top portion or proximal end portion 110a thereof, and is located above flex spool assembly 160. Fan 150 is a radial blower fan, as shown in FIG. 16A. In some embodiments, as shown in FIG. 16B, fan 150 may be in the form of an axial fan. It is contemplated that any other suitable fans may be used, such as, for example, centrifugal fans, diaphragm or piston actuated air pumps, peristaltic pumps, thermal chimney, centrifugal pumps, venturi pumps implemented via an air compressor, or the like. Fan 150 sits atop flex spool assembly 160 and is in fluid communication with central cavity 162 of flex spool assembly 160 such that fan 150 receives or draws air from central cavity 162 of flex spool assembly 160 such that the air passes through channels 119 of IDU 110. Fan 150 generates negative pressure within cavity 208 of first end portion 200a of drape 200 to draw air into drape 200.

Fan 150 may be coupled to or be in communication with a processor, for example, control device 4 (FIG. 1). Fan 150 may also be in communication with temperature sensors, integrated circuits, central processing units, motors, resistors, strain gauges, thermistors, or pressure sensors disposed within any of the components of surgical assembly 100 or in drapes 200, 300, or 400. Control device 4 is configured to adjust a speed of fan 150 based on an orientation of robotic arm 2. For example, if robotic arm 2 is in a collapsed state in which robotic arm 2 has a reduced overall length, speed of fan 150 may be reduced due to a decreased distance air travels through one of drapes 200, 300, or 400. If robotic arm 2 is in an extended state in which robotic arm 2 has an increased overall length, speed of fan 150 may be increased to account for the greater distance air must travel through drapes 200, 300, or 400. The control device 4 can detect whether robotic arm 2 is in its collapsed or extended states using strain gauges attached at the joints of robotic arm 2.

Control device 4 may also be configured to adjust the speed of fan 150 based on the pressure or temperature sensed by pressure and temperature sensors. For example, the speed of fan 150 may be increased as temperature in drape 200, 300, or 400 increases and the speed of fan 150 may be decreased with a decrease in temperature. In some embodiments, the speed of fan 150 may also be adjusted based on the ambient temperature outside of drape 200, 300, or 400. The control device 4 can measure the temperature within the drapes 200, 300, or 400 using various sensors that provide feedback to control device 4 about various conditions of the drape. For example, drapes 200, 300, 400 may include thermal sensors disposed at various portions of drapes 200, 300, or 400.

In other embodiments, control device 4 may be in communication with sensors that sense the temperature of, or measure the current/power used by, components of surgical assembly 100, such as, for example, microprocessors, integrated components, motor controllers, sense resistors, strain gauges, or motor windings.

A top portion 113a of housing cover 113 may define a plurality of vents or slits 152 therein to allow for air to transfer out of IDU 110. Fan 150 is configured to generate negative pressure, which draws air through sterile interface module 112, into channels 119 defined in IDU 110, through motor assembly 114 and then flex spool assembly 160 and out of top portion 113a of housing cover 113 through slits 152 to cool electronics during operation thereof, and to maintain a constant negative pressure through IDU 110.

With reference to FIGS. 17A-20, as mentioned above, surgical assembly 100 may further include a sterile interface module 112 for selectively interconnecting the IDU 110 and the electromechanical surgical instrument 130. The electromechanical surgical instrument 130 may be laterally coupled (e.g., side-loaded) to, or laterally decoupled from, the sterile interface module 112 of the robotic surgical assembly 100. In general, the sterile interface module 112 functions to provide an interface between the bottom portion 110b (i.e., distal end) of instrument drive unit 110 and an electromechanical surgical instrument such as electromechanical surgical instrument 130. This interface advantageously maintains sterility, provides a means to transmit electrical communication between the IDU 110 and the electromechanical surgical instrument 130, provides structure configured to transfer rotational force from the IDU 110 to the electromechanical surgical instrument 130 for performing a function with the electromechanical surgical instrument 130, and/or provides structure to selectively attach/remove the electromechanical surgical instrument 130 to/from the IDU 110 (e.g., for rapid instrument exchange).

Sterile interface module 112 defines a plurality of openings 180 in a collar 182 thereof 112. Openings 180 are disposed circumferentially around collar 182 of sterile interface module 112. Collar 182 is configured to protrude distally from inlet 210 of drape 200, first inlet 310a of drape 300, or first inlet 410a of drape 400, so that air can pass into openings 180 of sterile interface module 112 and into drape 200, 300, or 400, depending on which drape is used. Sterile interface module 112 includes a central passageway 184 defined through a proximal surface thereof and is in fluid communication with openings 180 of sterile interface module 112. Central passageway 184 has a key-shaped configuration to assist in alignment and in defining a mating direction with bottom portion 110*b* of IDU 110. In some embodiments, central passageway 184 may assume any suitable symbolic shape.

Upon connecting sterile interface module 112 to bottom portion 110*b* (FIG. 14) of IDU 110, openings 117 defined through bottom portion 110*b* of IDU 110 are in fluid communication with central passageway 184 of sterile interface module 112. As such, air may be passed from outside of drape 200, 300, or 400, into sterile interface module 112 via openings 180 of sterile interface module 112, and into IDU 110 via openings 117 of IDU to cool the internal components of IDU 110, for example, motor assembly 114, elongated flex circuit boards 127, nexus 129, and/or flex spool assembly 160.

In operation, proximal portion 42 of surgical robotic arm 2 is coupled to cart 10, and instrument drive unit 110, having sterile interface module 112 attached thereto, is coupled to slide rail 40 of surgical robotic arm 2. Any of the drapes 200, 300, 400 described herein may be used to cover surgical robotic assembly 100, robotic arm 2, and cart 10. For example, drape 300 may be used to cover surgical assembly 100 (e.g., IDU 110, and a top portion of sterile interface module 112), surgical robotic arm 2, and handle portion 12 of cart 10.

In particular, outlet 318 of second end portion 300*b* of drape 300 is placed over surgical assembly 100 and pulled in a proximal direction to position surgical assembly 100, including slide rail 40, in cavity 308 of first end portion 300*a*, and elongate members 2*a*, 2*b*, 2*c* of surgical robotic arm 2 in conduit 312 of intermediate portion 300*c* of drape 300. Proximal movement of drape 300 along surgical robotic arm 2 is continued until the elastic band, draw string, hook and loop fastener, draw string, cinch line, bungee hooks, magnetic material, or the like, of second end portion 300*b* of drape 300 is passed over handle portion 12 of cart 10, thereby disposing handle portion 12 of cart 10 in cavity 316 of second end portion 300*b* of drape 300.

Also in use, collar 182 of sterile interface module 112 is passed through first inlet 310*a* of first end portion 300*a* of drape 300 to expose openings 180 defined in sterile interface module 112 to an environment exterior to drape 300. First inlet 310*a* of drape 300 is secured to sterile interface module 112 using a ring, for example, a plastic ring (not explicitly shown), provided in drape 300 that surrounds first inlet 310*a* or using an elastic band, hook and loop fastener, cinch line, bungee hooks, magnetic material, or the like that surrounds first inlet 310*a*. The ring of drape 300 allows for sterile interface module 112 to rotate relative to and within first inlet 310*a* of drape 300 while maintaining sterile interface module 112 axially fixed therein. Second end portion 300*b* of drape 300 may be secured to cart 10 by allowing the inwardly-oriented bias of the elastic band of second end portion 300*b* of drape 300 to engage handle portion 12 of cart 10 or by tightening a tie cord of second end portion 300*b* of drape 300 around post 14 of cart 10, depending on whether second end portion 300*b* of drape 300 has an elastic band and/or a tie cord.

With drape 300 covering each of surgical assembly 100, surgical robotic arm 2, and handle portion 12 of cart 10, surgical instrument 130 may be attached to sterile interface module 112. During operation of surgical assembly 100, fan 150 of IDU 110 and/or a fan of cart 10 may be activated to create an air pathway or negative pressure through drape 300. In particular, the fan 150 of IDU 110 initially creates a negative pressure in channels 119 of IDU 110, which drives air into openings 180 defined in collar 182 of sterile interface module 112. The air travels through openings 180 of sterile interface module 112, and into channels 119 of IDU 110 via central passageway 184 of sterile interface module 112. Upon the air passing through central passageway 184 of sterile interface module 112, the air passes through first inlet 310*a* of drape 300.

In addition to air traveling into drape 300 via first inlet 310*a*, air may also be passed into drape 300 via second inlet 310*b*. In particular, upon activating fan 150 of IDU 110, a negative pressure is created in channels 119 driving air into IDU 110 through side openings 131 defined in housing 113 of IDU 110 via first and second fluid pathways "F1," "F2" of second inlet 310*b*.

Upon air entering channels 119 of IDU 110, the air in IDU 110 absorbs heat generated by the internal components of IDU 110 (e.g., motor assembly 114, circuit boards 127, nexus 129, flex spool assembly 160, etc.) and out of IDU 110 via vents 152 of IDU 110. A fan of cart 10, a fan of robotic surgical arm 2, and/or a fan of second end portion 300*b* of drape 300, may also be activated to draw the warmed air away from cavity 308 of first end portion 300*a* of drape 300, through conduit 312 of intermediate portion 300*c* of drape 300, and out of second end portion 300*b* of drape 300 via outlet 318 of drape 300. If the internal components of IDU 110 reach a temperature above a threshold temperature, fan 150 of IDU 110 and/or any other fans attached to drape 300, robotic arm 2, or cart 10 may be increased in speed to cause air to flow at a faster rate through drape 300. Due to the fluid pathways defined through IDU 110 taking a tortuous pathway (e.g., twisting, turning, and generally non-linear) therethrough, it is possible for air to pass therethrough while preventing liquids from passing therethrough.

Figure 21:
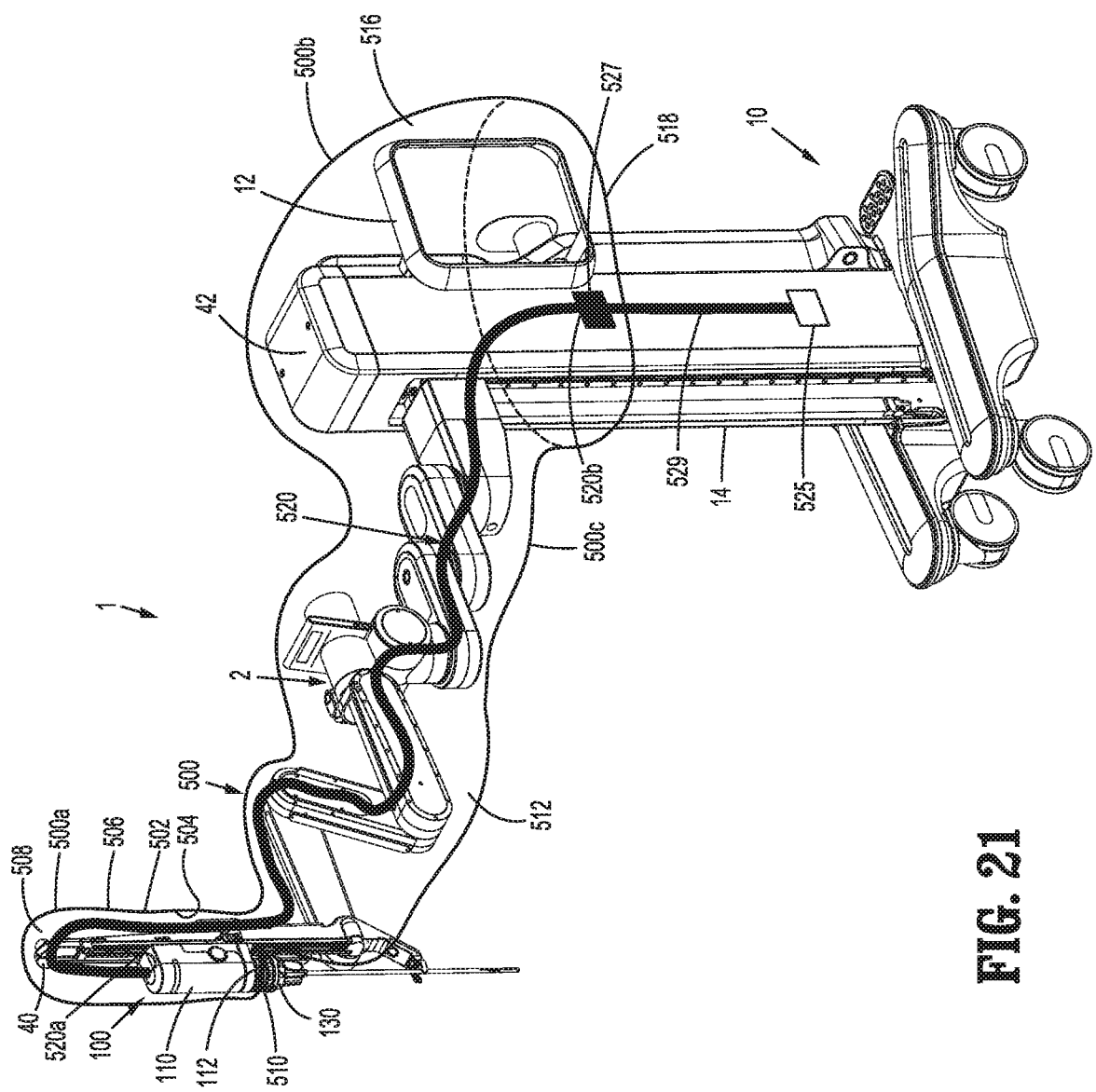
FIG. 21 is a perspective view of yet another embodiment of a drape covering the robotic surgical assembly, the robotic arm, and a portion of the robotic arm cart.

With reference to FIG. 21, yet another embodiment of a drape 500 for covering surgical assembly 100, surgical robotic arm 2, and portions of robotic arm cart 10, is provided. Drape 500 of FIG. 21 differs from the other drapes 200, 300, and 400 of the present disclosure by having a tubular member, such as, for example, a hose 520 extending along a length thereof. Hose 520 is configured to facilitate movement of warmed air from a first end portion 500*a* of drape 500 toward a second end portion 500*b* of drape 500 and out of drape 500.

Drape 500 includes a drape wall 506 having an outer surface 502 and an inner surface 504. The inner surface 504 at a first end portion 500*a* of drape 500 defines a cavity 508 therein. Cavity 508 of first end portion 500*a* of drape 500 is dimensioned to receive or encapsulate surgical assembly 100 (e.g., instrument drive unit 110 and slide rail 40). First end portion 500*a* of drape 500 defines an inlet or channel 510 extending through the outer surface 502 and the inner surface 504 of drape 500. Inlet 510 is in fluid communication with cavity 508 of first end portion 500*a*. As such, inlet 510 provides ingress of air flow into drape 500 to cool components of surgical assembly 500. Inlet 510 has a generally circular or annular shape dimensioned to form a seal with sterile interface module 112 of surgical assembly 100.

Intermediate portion 500*c* of drape 500 is dimensioned to encapsulate or house elongate members 2*a*, 2*b*, 2*c* of surgical robotic arm 2. In particular, intermediate portion 500*c* of drape 500 defines an elongated conduit 512 extending longitudinally therethrough and dimensioned for receipt of a surgical robotic arm, for example, robotic arm 2. Conduit 512 of intermediate portion 500*c* has a length dimensioned to accommodate robotic arm 2, in embodiments to accommodate at least an entire length of robotic arm 2 when robotic arm 2 has each of its elongate members 2*a*, 2*b*, 2*c* in an extended state.

Second end portion 500b of drape 500 defines a cavity 516 therein. Cavity 516 of second end portion 500b is dimensioned to receive or encapsulate at least proximal portion 42 of robotic arm 2 and/or a portion or portions of robotic cart 10. Second end portion 500b of drape 500 has an outlet 518 extending through drape wall 506 of drape 500. As such, outlet 518 of second end portion 500b is in fluid communication with cavity 516 of second end portion 500b of drape 500. Outlet 518 of drape 500 has a generally circular or annular shape dimensioned to fit over handle portion 12 of cart 10 or cart 10 in its entirety.

As mentioned above, drape 500 has a hose 520 integrated into drape wall 506 and running along a length thereof. Hose 520 is configured for passing air that has been warmed during operation of surgical assembly 100 (e.g., IDU 110) from first end portion 500a of drape 500 and out of drape 500 via outlet 518 at second end portion 500b. Hose 520 may be fabricated from a thermally-conductive material, such as, for example, woven metals, graphite, copper, or aluminum, to facilitate the transfer of heat out of drape 500. Hose 520 has a distal opening 520a and a proximal opening 520b and a central passageway (not explicitly shown) extending therebetween. Distal opening 520a of hose 520 is disposed within cavity 508 of first end portion 500a of drape 500 and proximal opening 520b is disposed outside of drape 500 adjacent second end portion 500b of drape 500. In some embodiments, proximal and distal openings 520a, 520b of hose 520 may be disposed at various locations of drape 500, for example, proximal opening 520b of hose 520 may be disposed within cavity 516 of second end portion 500b of drape 500 rather than outside of cavity 516. Distal opening 520a may be fitted onto fan 150 of IDU 110 such that air is pulled by and through fan 150 and into hose 520 via distal opening 520a.

Hose 520 of drape 500 may be attached to various portions of surgical assembly 100, robotic arm 2, and robotic arm cart 10 so that hose 520 travels along each of the portions of surgical assembly 100, robotic arm 2, and robotic arm cart 10, and moving heat away from each. For example, hose 520 may be attached to these components of surgical system 1 using a hook and loop fastener, clips, magnetic material, or the like. In some embodiments, instead of hose 520 being integrated into drape wall 506 of drape, hose 520 may be separate and apart from drape 520 and be attached to various portions of surgical assembly 100, robotic arm 2, and robotic arm cart 10 prior to these components being covered with drape 500.

Hose 520 may be configured to be coupled at proximal opening 520b thereof with a vacuum/pump 525 (e.g., any of the pumps/vacuums described above) for pulling air through hose 520. In particular, hose 520 may include an air hose plug 527 fluidly coupled to proximal opening 520b of hose 520 for coupling to an auxiliary air hose 529 extending from the vacuum/pump 525. Vacuum/pump 525 may be supported on cart 10 and disposed outside of drape 500. When air hose 529 is attached to air hose plug 525 of hose 520, an activation of vacuum/pump 525 will draw air through hose 520 to carry hot air that builds up in drape 500 out of drape 500.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. A robotic surgical system, comprising:
    a surgical robotic arm having a first end portion and a second end portion, the robotic arm being configured to move between a first orientation and a second orientation, in which the surgical robotic arm has a greater overall length than when the surgical robotic arm is in the first orientation;
    a surgical assembly coupled to the first end portion of the surgical robotic arm;
    a drape including:
        a first end portion having an outer surface and an inner surface and defining an inlet through the outer and inner surfaces, the first end portion defining a cavity therein dimensioned for receipt of the surgical assembly and being in fluid communication with the inlet;
        a second end portion having an outer surface and an inner surface and defining an outlet through the outer and inner surfaces of the second end portion, the second end portion defining a cavity therein and being in fluid communication with the outlet; and
        an intermediate portion extending between the first and second end portions and defining an elongated conduit therethrough dimensioned for receipt of the robotic arm;
    a fan configured to draw air through the inlet of the drape into the surgical assembly and out of the drape through the outlet thereof; and
    a controller in communication with the fan and configured to set the fan at a first speed when the surgical robotic arm is in the first orientation, and set the fan at a second speed when the surgical robotic arm is in the second orientation, the second speed being faster than the first speed, wherein the controller is configured to adjust the speed of the fan using measurements taken by strain gauges coupled at joints of the surgical robotic arm.

2. The robotic surgical system according to claim 1, further comprising a vent attached to the drape, wherein the controller is further configured to move the vent between open and closed configurations based on at least one of a temperature within the drape or the speed of the fan.

3. The robotic surgical system according to claim 1, wherein the surgical assembly includes an instrument drive unit having a first end portion and a second end portion, the fan attached to the first end portion.

4. The robotic surgical system according to claim 3, further comprising a sterile interface module coupled to the second end portion of the instrument drive unit, at least a portion of the sterile interface module being configured to be surrounded by the inlet of the drape to permit air to pass into the cavity of the first end portion of the drape via the sterile interface module.

5. The robotic surgical system according to claim 3, wherein the instrument drive unit has a plurality of fluid channels extending from the first end portion of the instrument drive unit to the second end portion of the instrument drive unit, the plurality of fluid channels taking a tortuous pathway through the instrument drive unit such that ingress of liquids is prevented and ingress of air is allowed.

6. The robotic surgical system according to claim 1, further comprising a robotic cart having a first end portion and a second end portion, wherein the cavity of the second end portion of the drape is dimensioned to receive at least one of the first or second end portions of the robotic cart.

7. The robotic surgical system according to claim 6, wherein the robotic cart has a fan that directs air flow in a direction from the first end portion of the drape toward the second end portion of the drape through the conduit of the drape.

8. The robotic surgical system according to claim 1, wherein the drape includes at least one elongated conductive rib extending along an inner surface of the intermediate portion of the drape.

9. The robotic surgical system according to claim 1, wherein the inlet of the drape is annular and dimensioned to surround a distal end portion of a sterile interface module of the surgical assembly.

10. The robotic surgical system according to claim 1, wherein the first end portion of the drape includes a patch covering the inlet, and wherein the patch is configured to permit ingress of air into the inlet.

11. The robotic surgical system according to claim 10, wherein the patch is fabricated from a nonwoven spun bonded olefin fiber material.

12. The robotic surgical system according to claim 1, wherein the first end portion of the drape includes:
    a first flap extending from the outer surface of the first end portion and overlapping with the inlet to define a first portion of a fluid pathway; and
    a second flap extending from the outer surface of the first end portion and overlapping with the first flap to define a second portion of the fluid pathway.

13. The robotic surgical system according to claim 12, wherein the first and second portions of the fluid pathway are parallel with one another and in fluid communication with one another.

14. The robotic surgical system according to claim 12, wherein the first end portion of the drape includes a fluid-resistant, porous material attached to the outer surface of the first end portion of the drape and covering the inlet.

15. The robotic surgical system according to claim 12, wherein the first end portion of the drape includes:
    a first rib disposed in and extending parallel with the first portion of the fluid pathway to maintain a spacing between the first flap and the outer surface thereof; and
    a second rib disposed in and extending parallel with the second portion of the fluid pathway to maintain a spacing between the first and second flaps.

16. The robotic surgical system according to claim 1, wherein the drape includes a tubular member extending along the intermediate portion thereof and having a proximal opening disposed within the first end portion of the drape and a distal opening disposed adjacent the second end portion of the drape such that air travels into the tubular member from the first end portion of the drape via the proximal opening and exits the tubular member via the distal opening.

17. A robotic surgical system, comprising:
    a surgical robotic arm having a first end portion and a second end portion, the robotic arm being configured to move between a first orientation and a second orientation;
    a surgical assembly coupled to the first end portion of the surgical robotic arm;
    a drape having outer and inner surfaces, the drape including:
        a first end portion defining an inlet through the outer and inner surfaces, the first end portion defining a cavity therein dimensioned for receipt of the surgical assembly and being in fluid communication with the inlet;
        a second end portion defining an outlet through the outer and inner surfaces, the second end portion defining a cavity therein and being in fluid communication with the outlet; and
        an intermediate portion extending between the first and second end portions and defining an elongated conduit therethrough dimensioned for receipt of the surgical robotic arm;
    a fan configured to draw air through the inlet of the drape into the surgical assembly and out of the drape through the outlet thereof; and
    a controller in communication with the fan and configured to set the fan at a first speed when the surgical robotic arm is in the first orientation, and set the fan at a second speed when the surgical robotic arm is in the second orientation, the second speed being faster than the first speed, wherein the controller is configured to adjust the speed of the fan using measurements taken by strain gauges coupled at joints of the surgical robotic arm.

18. A robotic surgical system, comprising:
    a surgical robotic arm having a first end portion and a second end portion, the robotic arm being configured to move between a first orientation and a second orientation;
    a drape having outer and inner surfaces, the drape including:
        a first end portion defining an inlet through the outer and inner surfaces, the first end portion configured for receipt of a surgical assembly;
        a second end portion defining an outlet through the outer and inner surfaces; and
        an intermediate portion extending between the first and second end portions and defining an elongated conduit therethrough dimensioned for receipt of the surgical robotic arm;
    a fan configured to draw air through the inlet of the drape into the surgical assembly and out of the drape through the outlet thereof; and
    a controller in communication with the fan and configured to set the fan at a first speed when the surgical robotic arm is in the first orientation, and set the fan at a second speed when the surgical robotic arm is in the second orientation, the second speed being faster than the first speed, wherein the controller is configured to adjust the speed of the fan using measurements taken by strain gauges coupled at joints of the surgical robotic arm.

* * * * *